(12) United States Patent
Faeh et al.

(10) Patent No.: US 7,674,815 B2
(45) Date of Patent: Mar. 9, 2010

(54) HETEROARYL AND BENZYL AMIDE COMPOUNDS

(75) Inventors: Christoph Faeh, Zurich (CH); Holger Kuehne, Grenzach-Wyhlen (DE); Thomas Luebbers, Loerrach (DE); Patrizio Mattei, Riehen (CH); Cyrille Maugeais, Mulhouse (FR); Philippe Pflieger, Schwoben (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/699,589

(22) Filed: Jan. 29, 2007

(65) Prior Publication Data

US 2007/0185113 A1    Aug. 9, 2007

(30) Foreign Application Priority Data

Feb. 7, 2006    (EP)    ................... 06101372

(51) Int. Cl.
  A61K 31/381    (2006.01)
  A61K 31/404    (2006.01)
  C07D 209/04    (2006.01)
  C07D 409/02    (2006.01)
  C07D 409/12    (2006.01)

(52) U.S. Cl. ................ 514/414; 514/444; 514/443; 514/419; 548/492; 548/503; 549/57; 549/59

(58) Field of Classification Search .......... 514/443, 514/444, 414, 419; 548/492, 503; 549/57, 549/59
See application file for complete search history.

(56) References Cited

U.S. PATENT DOCUMENTS 7,259,183 B2 * 8/2007 Conte-Mayweg et al. ... 514/419

2003/0191306 A1    10/2003  Sikorski et al.

FOREIGN PATENT DOCUMENTS

| WO | WO 95/30676 | 11/1995 |
| WO | WO 00/17166 A1 | 3/2000 |
| WO | WO 2005/002577 | 1/2005 |
| WO | WO 2005/100298 A1 | 10/2005 |
| WO | WO 2006/013048 A1 | 2/2006 |

OTHER PUBLICATIONS

Clarke et al., J. Chem. Soc.(C), pp. 1013-1016 (1970).
Doherty et al., J. Med. Chem., 48, pp. 71-90 (2005).
Renslo et al., J. Org. Chem., 63, pp. 7840-7850 (1998).
Yoshimura et al., J. Med. Chem., 43, pp. 2929-2937 (2000).
Le Goff et al., Pharmacology & Therapeutics, 101, pp. 17-38 (2004).
Okamoto et al., Nature, 406, 203-207 (2000).
Unangst et al., J. Heterocycl. Chem., 16, pp. 661-666 (1979).
Ansar et al., Eur. J. Med. Chem., 31, pp. 449-460 (1996).

* cited by examiner

*Primary Examiner*—Yong Chu
(74) *Attorney, Agent, or Firm*—George W. Johnston; Dennis P. Tramaloni; Brian C. Remy

(57) ABSTRACT

Compounds of formula I

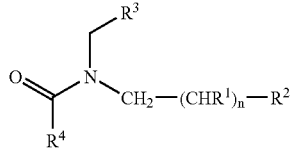

(I)

processes for their preparation, their use as pharmaceuticals and to pharmaceutical compositions comprising them.

20 Claims, No Drawings

HETEROARYL AND BENZYL AMIDE COMPOUNDS

PRIORITY TO RELATED APPLICATIONS

This application claims the benefit of European Application No. 06101372.8, filed Feb. 7, 2006, which is hereby incorporated by reference in its entirety.

The present invention relates to novel benzamide and heteroarene derivatives, processes for their preparation, their use as pharmaceuticals and to pharmaceutical compositions comprising them.

More particularly, the present invention provides in a first aspect a compound of formula

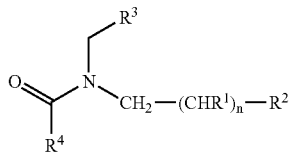

(I)

wherein $R^1$ is hydrogen, $C_1$-$C_6$alkyl, hydroxy or halogen;

$R^2$ is hydrogen, $C_1$-$C_6$alkyl, halogen-$C_1$-$C_6$alkyl, $C_2$-$C_6$alkenyl, heterocyclyl, unsubstituted aryl or aryl substituted by one or more substituents selected from halogen, $C_1$-$C_6$alkyl and halogen-$C_1$-$C_6$alkyl, —$OR^6$, wherein $R^6$ is $C_1$-$C_6$alkyl, halogen-$C_1$-$C_6$alkyl or phenyl, —$NR^7R^8$, wherein $R^7$ and $R^8$ independently are hydrogen, $C_1$-$C_6$alkyl or phenyl, or —C(O)—$OR^9$, wherein $R^9$ is hydrogen or $C_1$-$C_6$alkyl;

$R^3$ is unsubstituted heteroaryl or heteroaryl substituted by one or more substituents selected from halogen, $C_1$-$C_6$alkyl, halogen-$C_1$-$C_6$alkyl, $C_3$-$C_8$cycloalkyl and halogen-$C_3$-$C_8$cycloalkyl;

$R^4$ is a group (a)

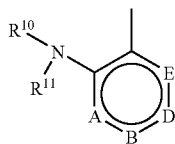

wherein

A is $CR^{17}$ or N, wherein $R^{17}$ is hydrogen, halogen, $C_1$-$C_6$alkyl, $C_1$-$C_6$alkoxy or $C_2$-$C_6$alkenyl;

B is $CR^{18}$ or N, wherein $R^{18}$ is hydrogen, halogen, $C_1$-$C_6$alkyl, $C_1$-$C_6$alkoxy or $C_2$-$C_6$alkenyl;

D is $CR^{19}$ or N, wherein $R^{19}$ is hydrogen, halogen, $C_1$-$C_6$alkyl, $C_1$-$C_6$alkoxy, $C_2$-$C_6$alkenyl or phenyl;

E is $CR^{20}$ or N, wherein $R^{20}$ is hydrogen, halogen, $C_1$-$C_6$alkyl, $C_1$-$C_6$alkoxy or $C_2$-$C_6$alkenyl;

$R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$aklylene; or, when A is $CR^{17}$, $R^{11}$ and $R^{17}$ together are —CH=CH—, —$CH_2$—$CH_2$— or —N=CH—; and n is 1, 2 or 3;

and all pharmaceutically acceptable salts thereof.

Examples of $C_1$-$C_6$alkyl include branched and straight-chain monovalent saturated aliphatic hydrocarbon radicals of one to six carbon atoms, e.g. methyl, ethyl, propyl, isopropyl, butyl, isobutyl, tert.-butyl, the isomeric pentyls and the isomeric hexyls.

Examples of halogen include fluorine, chlorine, bromine and iodine.

Examples of halo-$C_1$-$C_6$alkyl include alkyl groups as defined above wherein at least one of the hydrogen atoms of the alkyl group is replaced by a halogen atom, e.g. fluoro or chloro, e.g. trifluoromethyl, difluoromethyl, fluoromethyl, 1,2,2,2-tetrafluoro-1-trifluoromethyl-ethyl, pentafluoroethyl and chlorodifluoromethyl.

Examples of $C_3$-$C_8$cycloalkyl include saturated carbocyclic groups containing from 3 to 8 carbon atoms, such as cyclopropyl, cyclobutyl, cyclopentyl, cyclohexyl, cycloheptyl and cyclooctyl.

Examples for alkenyl, alone or in combination, include straight-chain or branched hydrocarbon radicals comprising an olefinic bond and up to 6, e.g., up to 4 carbon atoms, e.g. ethenyl, 1-propenyl, 2-propenyl, isopropenyl, 1-butenyl, 2-butenyl, 3-butenyl and isobutenyl.

Examples of aryl include phenyl and naphthyl.

Heterocyclic groups may be saturated or unsaturated and may contain one or more additional heterocyclic atoms, e.g. nitrogen, oxygen or sulfur.

Phenyl and heteroaryl may be annulated with a saturated or unsaturated moiety to form a bicyclic group.

Examples for an unsaturated heterocyclic group include a heteroaryl group like pyridinyl, pyridazinyl, pyrimidinyl, thiazolyl, oxazolyl, isothiazolyl, isoxazolyl, thiophenyl, furanyl, pyrazolyl, indolyl, benzo[b]thiophenyl, 4,5,6,7-tetrahydro-benzo[b]thiophenyl, benzofuranyl, 4,5,6,7-tetrahydrobenzothiazolyl, e.g. aminopyridinyl, aminopyridazinyl, aminopyrimidinyl, aminothiophenyl, aminopyrazolyl, aminothiazolyl, aminoisothiazolyl, aminoisoxazolyl, e.g. 2-aminopyridin-3-yl, 3-aminopyridin-2-yl, 4-aminopyridin-3-yl, 3-aminopyridin-4-yl, 3-amino-pyridazin-2-yl, 4-aminopyridazin-3-yl, 5-aminopyridazin-4-yl, 3-aminopyridazin-4-yl, 4-amino-pyrimidin-5-yl, 5-aminopyrimidin-4-yl, 5-aminothiazol-4-yl, 5-aminoisothiazol-4-yl and 3-aminoisoxazol-4-yl, 2-aminothiophen-3-yl, 3-aminothiophen-2-yl, 3-aminothiophen-4-yl, 5-aminopyrazol-4-yl and may be unsubstituted or substituted by one to three substituents selected from halogen, alkyl, halogenalkyl, cycloalkyl which may again be unsubstituted or substituted by one or more of the above mentioned substiutents.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as methanesulfonic acid, ethanesulfonic acid, p-toluenesulfonic acid, and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions.

Particularly preferred pharmaceutically acceptable salts of compounds of formula I are the hydrochloride salts.

The compounds of formula I can also be solvated, e.g. hydrated. The salvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In one embodiment the present invention provides compounds of formula I wherein $R^1$ is hydrogen.

In one embodiment the present invention provides compounds of formula I wherein $R^2$ is unsubstituted aryl or aryl substituted by one or more substituents selected from halogen, $C_1$-$C_6$alkyl, halogen-$C_1$-$C_6$alkyl and —$OR^6$, wherein $R^6$ is $C_1$-$C_6$alkyl, halogen-$C_1$-$C_6$alkyl or phenyl. In another embodiment the present invention provides compounds of formula I wherein $R^2$ is aryl substituted by one or two substituents selected from halogen, $C_1$-$C_6$alkyl and halogen-$C_1$-$C_6$alkyl.

In still another embodiment the present invention provides compounds of formula I wherein $R^2$ is phenyl substituted by one or two substituents selected from halogen, $C_1$-$C_6$alkyl and halogen-$C_1$-$C_6$alkyl, wherein the substituent is in 3 or 4 position or the substituents are in 3 and 4 position.

In one embodiment the present invention provides compounds of formula I wherein $R^3$ is heteroaryl selected from pyridinyl, thiazolyl, thiophenyl, indolyl, benzo[b]thiophenyl, 4,5,6,7-tetrahydro-benzo[b]thiophenyl, benzofuranyl and 4,5,6,7-tetrahydro-benzothiazolyl, which heteroaryl is unsubstituted or substituted by one or more substituents selected from halogen, $C_1$-$C_6$alkyl, halogen-$C_1$-$C_6$alkyl, $C_3$-$C_8$cycloalkyl and halogen-$C_3$-$C_8$cycloalkyl.

In one embodiment the present invention provides compounds of formula I wherein $R^4$ is a group (a) wherein -A-B-D-E- is —$CR^{17}$—$CR^{18}$—$CR^{19}$—$CR^{20}$— wherein $R^{17}$, $R^{18}$ and $R^{20}$ independently are hydrogen, halogen, $C_1$-$C_6$alkyl, $C_1$-$C_6$alkoxy or $C_2$-$C_6$alkenyl, and $R^{19}$ is hydrogen, halogen, $C_1$-$C_6$alkyl, $C_1$-$C_6$alkoxy, $C_2$-$C_6$alkenyl or phenyl; and $R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$alkylene; or $R^{11}$ and $R^{17}$ together are —CH=CH—, —$CH_2$—$CH_2$— or —N=CH—. In another embodiment the present invention provides compounds of formula I wherein $R^4$ is a group (a) wherein -A-B-D-E- is —$CR^{17}$—$CR^{18}$—$CR^{19}$—$CR^{20}$— wherein $R^{17}$, $R^{18}$ and $R^{20}$ independently are hydrogen, halogen, $C_1$-$C_6$alkyl, $C_1$-$C_6$alkoxy or $C_2$-$C_6$alkenyl, and $R^{19}$ is hydrogen, halogen, $C_1$-$C_6$alkyl, $C_1$-$C_6$alkoxy, $C_2$-$C_6$alkenyl or phenyl; $R^{10}$ is hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; and $R^{11}$ and $R^{17}$ together are —CH=CH—, —$CH_2$—$CH_2$— or —N=CH—. In still another embodiment the present invention provides compounds of formula I wherein $R^4$ is a group (a) wherein -A-B-D-E- is —$CR^{17}$—$CR^{18}$—$CR^{19}$—$CR^{20}$— wherein $R^{18}$, $R^{19}$ and $R^{20}$ independently are hydrogen or halogen; $R^{10}$ is hydrogen; and $R^{11}$ and $R^{17}$ together are —CH=CH—, —$CH_2$—$CH_2$— or —N=CH—.

In one embodiment the present invention provides a compound of formula I wherein $R^4$ is a group (a) wherein at least one of A, B, D and E is N.

In one embodiment the present invention provides a compound of formula I wherein $R^4$ is a group (a) wherein A is N, B is $CR^{18}$ or N, wherein $R^{18}$ is hydrogen, halogen, $C_1$-$C_6$alkyl, $C_1$-$C_6$alkoxy or $C_2$-$C_6$alkenyl; D is $CR^{19}$ or N, wherein $R^{19}$ is hydrogen, halogen, $C_1$-$C_6$alkyl, $C_1$-$C_6$alkoxy, $C_2$-$C_6$alkenyl or phenyl; E is $CR^{20}$ or N, wherein $R^{20}$ is hydrogen, halogen, $C_1$-$C_6$alkyl, $C_1$-$C_6$alkoxy or $C_2$-$C_6$alkenyl; $R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$alkylene. In another embodiment the present invention provides a compound of formula I wherein $R^4$ is a group (a) wherein A is N, B is $CR^{18}$, wherein $R^{18}$ is hydrogen, halogen, $C_1$-$C_6$alkyl, $C_1$-$C_6$alkoxy or $C_2$-$C_6$alkenyl; D is $CR^{19}$, wherein $R^{19}$ is hydrogen, halogen, $C_1$-$C_6$alkyl, $C_1$-$C_6$alkoxy, $C_2$-$C_6$alkenyl or phenyl; E is $CR^{20}$, wherein $R^{20}$ is hydrogen, halogen, $C_1$-$C_6$alkyl, $C_1$-$C_6$alkoxy or $C_2$-$C_6$alkenyl; $R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$alkylene. In still another embodiment the present invention provides a compound of formula I wherein $R^4$ is a group (a) wherein A is N, B is $CR^{18}$, wherein $R^{18}$ is hydrogen; D is $CR^{19}$, wherein $R^{19}$ is hydrogen or halogen; E is $CR^{20}$, wherein $R^{20}$ is hydrogen or halogen; $R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$alkylene.

In one embodiment the present invention provides a compound of formula I wherein $R^4$ is a group (a) wherein B is N, A is $CR^{17}$ or N, wherein $R^{17}$ is hydrogen, halogen, $C_1$-$C_6$alkyl, $C_1$-$C_6$alkoxy or $C_2$-$C_6$alkenyl; D is $CR^{19}$ or N, wherein $R^{19}$ is hydrogen, halogen, $C_1$-$C_6$alkyl, $C_1$-$C_6$alkoxy, $C_2$-$C_6$alkenyl or phenyl; E is $CR^{20}$ or N, wherein $R^{20}$ is hydrogen, halogen, $C_1$-$C_6$alkyl, $C_1$-$C_6$alkoxy or $C_2$-$C_6$alkenyl; $R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$alkylene, or, when A is $CR^{17}$, $R^{11}$ and $R^{17}$ together are —CH=CH—, —$CH_2$—$CH_2$— or —N=CH—. In another embodiment the present invention provides a compound of formula I wherein $R^4$ is a group (a) wherein B is N, A is $CR^{17}$, wherein $R^{17}$ is hydrogen, halogen, $C_1$-$C_6$alkyl, $C_1$-$C_6$alkoxy or $C_2$-$C_6$alkenyl; D is $CR^{19}$, wherein $R^{19}$ is hydrogen, halogen, $C_1$-$C_6$alkyl, $C_1$-$C_6$alkoxy, $C_2$-$C_6$alkenyl or phenyl; E is $CR^{20}$, wherein $R^{20}$ is hydrogen, halogen, $C_1$-$C_6$alkyl, $C_1$-$C_6$alkoxy or $C_2$-$C_6$alkenyl; $R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$alkylene, or, when A is $CR^{17}$, $R^{11}$ and $R^{17}$ together are —CH=CH—, —$CH_2$—$CH_2$— or —N=CH—. In still another embodiment the present invention provides a compound of formula I wherein $R^4$ is a group (a) wherein B is N, A is $CR^{17}$, wherein $R^{17}$ is hydrogen; D is $CR^{19}$, wherein $R^{19}$ is hydrogen or halogen; E is $CR^{20}$, wherein R is hydrogen or halogen; $R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$alkylene, or, when A is $CR^{17}$, $R^{11}$ and $R^{17}$ together are —CH=CH—, —$CH_2$—$CH_2$— or —N=CH—.

In one embodiment the present invention provides compounds of formula I wherein n is 1.

In one embodiment the present invention provides compounds of formula I wherein
$R^1$ is hydrogen;
$R^2$ is unsubstituted aryl or aryl substituted by one or more substituents selected from halogen, $C_1$-$C_6$alkyl and halogen-$C_1$-$C_6$alkyl;
$R^3$ is unsubstituted heteroaryl or heteroaryl substituted by one or more substituents selected from halogen, $C_1$-$C_6$alkyl and halogen-$C_1$-$C_6$alkyl;
$R^4$ is a group (a)

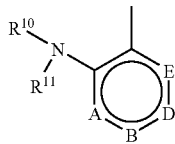

wherein
A is $CR^{17}$ or N, wherein $R^{17}$ is hydrogen, halogen, $C_1$-$C_6$alkyl, $C_1$-$C_6$alkoxy or $C_2$-$C_6$alkenyl;
B is $CR^{18}$ or N, wherein $R^{18}$ is hydrogen, halogen, $C_1$-$C_6$alkyl, $C_1$-$C_6$alkoxy or $C_2$-$C_6$alkenyl;
D is $CR^{19}$ or N, wherein $R^{19}$ is hydrogen, halogen, $C_1$-$C_6$alkyl, $C_1$-$C_6$alkoxy, $C_2$-$C_6$alkenyl or phenyl;
E is $CR^{20}$ or N, wherein $R^{20}$ is hydrogen, halogen, $C_1$-$C_6$alkyl, $C_1$-$C_6$alkoxy or $C_2$-$C_6$alkenyl;
$R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$alkylene; or, when A is $CR^{17}$,
$R^{11}$ and $R^{17}$ together are —CH=CH—, —$CH_2$—$CH_2$— or —N=CH—; and
n is 1, 2 or 3;

and all pharmaceutically acceptable salts thereof.

In one embodiment the present invention provides compounds of formula I wherein
$R^1$ is hydrogen, $C_1$-$C_6$alkyl, hydroxy or halogen;
$R^2$ is hydrogen, $C_1$-$C_6$alkyl, halogen-$C_1$-$C_6$alkyl, $C_2$-$C_6$alkenyl, heterocyclyl, unsubstituted aryl or aryl substituted by one or more substituents selected from halogen, $C_1$-$C_6$alkyl and halogen-$C_1$-$C_6$alkyl, —$OR^6$, wherein $R^6$ is $C_1$-$C_6$alkyl or phenyl, —$NR^7R^8$, wherein $R^7$ and $R^8$ independently are hydrogen, $C_1$-$C_6$alkyl or phenyl, or —C(O)—$OR^9$, wherein $R^9$ is hydrogen or $C_1$-$C_6$alkyl;
$R^3$ is unsubstituted heteroaryl or heteroaryl substituted by one or more substituents selected from halogen, $C_1$-$C_6$alkyl and halogen-$C_1$-$C_6$alkyl, wherein heteroaryl is selected from pyridinyl, thiazolyl, thiophenyl, indolyl, benzo[b]thiophenyl, 4,5,6,7-tetrahydro-benzo[b]thiophenyl, benzofuranyl and 4,5,6,7-tetrahydro-benzothiazolyl;

$R^4$ is a group (a)

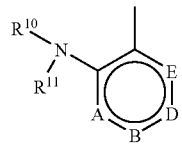

wherein
A is $CR^{17}$ or N, wherein $R^{17}$ is hydrogen, halogen, $C_1$-$C_6$alkyl, $C_1$-$C_6$alkoxy or $C_2$-$C_6$alkenyl;
B is $CR^{18}$ or N, wherein $R^{18}$ is hydrogen, halogen, $C_1$-$C_6$alkyl, $C_1$-$C_6$alkoxy or $C_2$-$C_6$alkenyl;
D is $CR^{19}$ or N, wherein $R^{19}$ is hydrogen, halogen, $C_1$-$C_6$alkyl, $C_1$-$C_6$alkoxy, $C_2$-$C_6$alkenyl or phenyl;
E is $CR^{20}$ or N, wherein $R^{20}$ is hydrogen, halogen, $C_1$-$C_6$alkyl, $C_1$-$C_6$alkoxy or $C_2$-$C_6$alkenyl;
$R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$alkylene; or, when A is $CR^{17}$,
$R^{11}$ and $R^{17}$ together are —CH=CH—, —$CH_2$—$CH_2$— or —N=CH—; and
n is 1, 2 or 3;

and all pharmaceutically acceptable salts thereof.

In one embodiment the present invention provides compounds of formula I wherein
$R^1$ is hydrogen;
$R^2$ is unsubstituted aryl or aryl substituted by one or more substituents selected from halogen, $C_1$-$C_6$alkyl and halogen-$C_1$-$C_6$alkyl;
$R^3$ is unsubstituted heteroaryl or heteroaryl substituted by one or more substituents selected from halogen, $C_1$-$C_6$alkyl and halogen-$C_1$-$C_6$alkyl, wherein heteroaryl is selected from pyridinyl, thiazolyl, thiophenyl, indolyl, benzo[b]thiophenyl, 4,5,6,7-tetrahydro-benzo[b]thiophenyl, benzofuranyl and 4,5,6,7-tetrahydro-benzothiazolyl;
$R^4$ is a group (a) wherein -A-B-D-E- is —$CR^{17}$=$CR^{18}$—$CR^{19}$=$CR^{20}$— wherein $R^{17}$, $R^{18}$ and $R^{20}$ independently are hydrogen, halogen, $C_1$-$C_6$alkyl, $C_1$-$C_6$alkoxy or $C_2$-$C_6$alkenyl, and $R^{19}$ is hydrogen, halogen, $C_1$-$C_6$alkyl, $C_1$-$C_6$alkoxy, $C_2$-$C_6$alkenyl or phenyl; and $R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$alkylene; or $R^{11}$ and $R^{17}$ together are —CH=CH—, —$CH_2$—$CH_2$— or —N=CH—; and
n is 1, 2 or 3;

and all pharmaceutically acceptable salts thereof.

In one embodiment the present invention provides compounds of formula I wherein
$R^1$ is hydrogen;
$R^2$ is unsubstituted aryl or aryl substituted by one or more substituents selected from halogen, $C_1$-$C_6$alkyl and halogen-$C_1$-$C_6$alkyl;
$R^3$ is unsubstituted heteroaryl or heteroaryl substituted by one or more substituents selected from halogen, $C_1$-$C_6$alkyl and halogen-$C_1$-$C_6$alkyl, wherein heteroaryl is selected from pyridinyl, thiazolyl, thiophenyl, indolyl, benzo[b]thiophenyl, 4,5,6,7-tetrahydro-benzo[b]thiophenyl, benzofuranyl and 4,5,6,7-tetrahydro-benzothiazolyl;
$R^4$ is a group (a) wherein A is N, B is $CR^{18}$ or N, wherein $R^{18}$ is hydrogen, halogen, $C_1$-$C_6$alkyl, $C_1$-$C_6$alkoxy or $C_2$-$C_6$alkenyl; D is $CR^{19}$ or N, wherein $R^{19}$ is hydrogen, halogen, $C_1$-$C_6$alkyl, $C_1$-$C_6$alkoxy, $C_2$-$C_6$alkenyl or phenyl; E is $CR^{20}$ or N, wherein $R^{20}$ is hydrogen, halogen, $C_1$-$C_6$alkyl, $C_1$-$C_6$alkoxy or $C_2$-$C_6$alkenyl; $R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$alkylene; and n is 1, 2 or 3;

and all pharmaceutically acceptable salts thereof.

In one embodiment the present invention provides compounds of formula I wherein $R^1$ is hydrogen;

$R^2$ is unsubstituted aryl or aryl substituted by one or more substituents selected from halogen, $C_1$-$C_6$alkyl and halogen-$C_1$-$C_6$alkyl;

$R^3$ is unsubstituted heteroaryl or heteroaryl substituted by one or more substituents selected from halogen, $C_1$-$C_6$alkyl and halogen-$C_1$-$C_6$alkyl, wherein heteroaryl is selected from pyridinyl, thiazolyl, thiophenyl, indolyl, benzo[b]thiophenyl, 4,5,6,7-tetrahydro-benzo[b]thiophenyl, benzofuranyl and 4,5,6,7-tetrahydro-benzothiazolyl;

$R^4$ is a group (a) wherein B is N, A is $CR^{17}$ or N, wherein $R^{17}$ is hydrogen, halogen, $C_1$-$C_6$alkyl, $C_1$-$C_6$alkoxy or $C_2$-$C_6$alkenyl; D is $CR^{19}$ or N, wherein $R^{19}$ is hydrogen, halogen, $C_1$-$C_6$alkyl, $C_1$-$C_6$alkoxy, $C_2$-$C_6$alkenyl or phenyl; E is $CR^{20}$ or N, wherein $R^{20}$ is hydrogen, halogen, $C_1$-$C_6$alkyl, $C_1$-$C_6$alkoxy or $C_2$-$C_6$alkenyl; $R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$alkylene, or, when A is $CR^{17}$, $R^{11}$ and $R^{17}$ together are —CH=CH—, —$CH_2$—$CH_2$— or —N=CH—; and n is 1, 2 or 3;

and all pharmaceutically acceptable salts thereof.

In addition to the foregoing the present invention also provides a process for the production of a compound of formula I

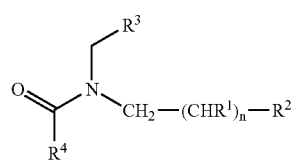

(I)

wherein $R^1$ is hydrogen, $C_1$-$C_6$alkyl, hydroxy or halogen;

$R^2$ is hydrogen, $C_1$-$C_6$alkyl, halogen-$C_1$-$C_6$alkyl, $C_2$-$C_6$alkenyl, heterocyclyl, unsubstituted aryl or aryl substituted by one or more substituents selected from halogen, $C_1$-$C_6$alkyl and halogen-$C_1$-$C_6$alkyl, —$OR^6$, wherein $R^6$ is $C_1$-$C_6$alkyl, halogen-$C_1$-$C_6$alkyl or phenyl, —$NR^7R^8$, wherein $R^7$ and $R^8$ independently are hydrogen, $C_1$-$C_6$alkyl or phenyl, or —C(O)—$OR^9$, wherein $R^9$ is hydrogen or $C_1$-$C_6$alkyl;

$R^3$ is unsubstituted heteroaryl or heteroaryl substituted by one or more substituents selected from halogen, $C_1$-$C_6$alkyl, halogen-$C_1$-$C_6$alkyl, $C_3$-$C_8$cycloalkyl and halogen-$C_3$-$C_8$cycloalkyl;

$R^4$ is a group (a)

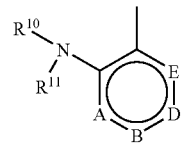

wherein

A is $CR^{17}$ or N, wherein $R^{17}$ is hydrogen, halogen, $C_1$-$C_6$alkyl, $C_1$-$C_6$alkoxy or $C_2$-$C_6$alkenyl;

B is $CR^{18}$ or N, wherein $R^{18}$ is hydrogen, halogen, $C_1$-$C_6$alkyl, $C_1$-$C_6$alkoxy or $C_2$-$C_6$alkenyl;

D is $CR^{19}$ or N, wherein $R^{19}$ is hydrogen, halogen, $C_1$-$C_6$alkyl, $C_1$-$C_6$alkoxy, $C_2$-$C_6$alkenyl or phenyl;

E is $CR^{20}$ or N, wherein $R^{20}$ is hydrogen, halogen, $C_1$-$C_6$alkyl, $C_1$-$C_6$alkoxy or $C_2$-$C_6$alkenyl;

$R^{10}$ and $R^{11}$ are independently hydrogen, halogen, $C_1$-$C_6$alkyl, COR wherein R is $C_1$-$C_6$alkyl, $C_1$-$C_6$alkoxy or $C_3$-$C_6$cycloalkyl, $S(O)_2$—$C_1$-$C_6$alkyl, $C_3$-$C_6$cycloalkyl, or phenyl; or together are $C_1$-$C_6$alkylene; or, when A is $CR^{17}$, $R^{11}$ and $R^{17}$ together are —CH=CH—, —$CH_2$—$CH_2$— or —N=CH—; and n is 1, 2 or 3;

and all pharmaceutically acceptable salts thereof;

which process comprises reacting an acid derivative, a compound of formula II

(II)

wherein $R^4$ has the above meanings and W is hydroxy, OLi, ONa, OK or halogen, e.g. Cl, with a secondary amine derivative, a compound of formula III

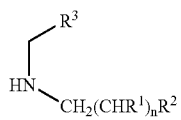

(III)

wherein $R^1$, $R^2$, $R^3$ and n have the above meanings.

If carboxylic acids (W=OH) or carboxylate salts (W=OLi, ONa, OK) of formula II are used in this process, standard peptide coupling reagents can be applied to activate the acid prior to the coupling reaction. Typically, the acid derivative II (R=OH, OLi, ONa, OK) is mixed with a coupling reagent such as EDC or EDC.HCl, DCC, HBTU or TBTU in an inert solvent such as N,N-dimethylformamide, dimethylacetamide (DMA) or dichloromethane (DCM) together with the appropriate secondary amine derivative III. Optionally a base (e.g. N,N-diisopropylethyl amine, triethylamine, N-methyl morpholine) and/or 1-hydroxybenzotriazole (HOBT) can be added. The reaction mixture is stirred for 1 to 24 h at a temperature of about −30° C. to about 70° C. (e.g. ambient temperature).

Alternatively, acid chlorides (W=Cl) can be reacted with secondary amine derivatives III to obtain formula (I) compounds, using standard protocols.

Acid derivatives of formula II are commercially available or can be prepared as described in the example section.

Secondary amines of the general formula III can be synthesized by standard methods. They may be synthesized as outlined below.

Compounds of formula III

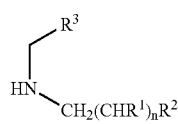
(III)

wherein $R^1$, $R^2$, $R^3$ and n have the above meanings;

may be prepared by reductive amination of a benzaldehyde derivative, a compound of formula IV

(IV)

wherein $R^3$ is as defined above, with an amine, a compound of formula V

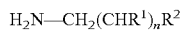
(V)

wherein $R^1$, $R^2$ and n are as defined above.

The necessary starting amines and aldehydes are commercially available or are synthesized using standard methods as e.g. described in the example section.

Secondary amines III may alternatively be synthesized by reduction of amide derivatives, compounds of formula VII

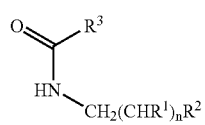
(VII)

wherein $R^1$, $R^2$, $R^3$ and n are as defined above, using methods and reagents know in the art.

Amide derivatives, compounds of formula VII are available by the coupling of acid derivatives, compounds of formula VI

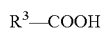
(VI)

wherein $R^3$ is as defined above, with a compound of formula V.

The necessary starting acids are commercially available or may be synthesized using standard methods as e.g. described in the example section.

The salt forms are made by standard procedures known to the skilled artisan.

In general, the nomenclature used in this Application is based on AUTONOM™ v.4.0, a Beilstein Institute computerized system for the generation of IUPAC systematic nomenclature.

The following abbreviations are used: RT: room temperature; HBTU: N,N,N',N'-tetra-methyl-O-(benzotriazol-1-yl) uronium hexafluorophosphate; THF: tetrahydrofuran; DMF: N,N-dimethylformamide.

EXAMPLE 1

Preparation of 5-chloro-1H-indole-7-carboxylic acid benzofuran-2-ylmethyl-[2-(3,4-dichloro-phenyl)-ethyl]-amide To a solution of 72 mg (0.37 mmol) of 5-chloro-1H-indole-7-carboxylic acid and 118 mg (0.37 mmol) of benzofuran-2-ylmethyl-[2-(3,4-dichloro-phenyl)-ethyl]-amine in DMF (5 ml) were added 131 mg (0.41 mmol) of TBTU and 126 µl (0.74 mmol) of N,N-diisopropylethyl amine and the mixture was stirred over night at RT. Then the reaction mixture was diluted with ethyl acetate and washed with water, brine, sat. $NaHCO_3$ solution, 1N HCl and again with brine. The organic layer was then dried ($MgSO_4$) and concentrated. The remaining residue was purified by column chromatography (silica gel; ethyl acetate/cyclohexane 9:1) to yield the title compound as a yellow oil (145 mg, 79%). MS (ISP) 497.3 $(M+H)^+$.

EXAMPLE 2

Preparation of 5-chloro-1H-indole-7-carboxylic acid benzo[b]thiophen-2-ylmethyl-[2-(3,4-dichloro-phenyl)-ethyl]-amide In analogy to example 1, 129 mg (77%) of the title compound were obtained as a colorless solid starting from 64 mg (0.33 mmol) of 5-chloro-1H-indole-7-carboxylic acid and 109 mg (0.33 mmol) of benzo[b]thiophen-2-ylmethyl-[2-(3,4-dichloro-phenyl)-ethyl]-amine. $^{1H}$NMR ($CDCl_3$, 300 MHz): δ 2.83 (t, J=7.2 Hz, 2H), 3.71 (t, J=7.2 Hz, 2H), 4.87 (s, 2H), 6.43 (m, 1H), 6.80 (br s, 1H), 7.07 (br s, 1H), 7.15 (m, 4H), 7.28 (m, 2H), 7.61 (d, J=1.7 Hz, 1H), 7.67 (dd, J=6.6 and 2.0 Hz, 1H), 7.74 (dd, J=6.6 and 1.9 Hz, 1H), 8.75 (br s, 1H).

EXAMPLE 3

Preparation of 5-chloro-1H-indole-7-carboxylic acid [2-(3,4-dichloro-phenyl)-ethyl]-(6,7-dimethyl-benzofuran-2-ylmethyl)-amide In analogy to example 1, 50 mg (51%) of the title compound was obtained as a colorless foam starting from 36 mg (0.19 mmol) of 5-chloro-1H-indole-7-carboxylic acid and 65 mg (0.19 mmol) of [2-(3,4-dichloro-phenyl)-ethyl]-(6,7-dimethyl-benzofuran-2-ylmethyl)-amine. MS (ISP) 523.2 $(M-H)^-$.

EXAMPLE 4

Preparation of 5-chloro-1H-indole-7-carboxylic acid (5,7-dichloro-benzofuran-2-ylmethyl)-[2-(3,4-dichloro-phenyl)-ethyl]-amide In analogy to example 1, 33 mg (40%) of the title compound was obtained as a colorless foam starting from 29 mg (0.15 mmol) of 5-chloro-1H-indole-7-carboxylic acid and 57 mg (0.15 mmol) of (5,7-dichloro-benzofuran-2-ylmethyl)-[2-(3,4-dichloro-phenyl)-ethyl]-amine. MS (ISP) 567.2 $(M+H)^+$.

EXAMPLE 5

Preparation of 5-chloro-1H-indole-7-carboxylic acid [2-(3,4-dichloro-phenyl)-ethyl]-(5-methyl-benzofuran-2-ylmethyl)-amide In analogy to example 1, 147 mg (83%) of the title compound were obtained as a colorless foam starting from 68 mg (0.35 mmol) of 5-chloro-1H-indole-7-carboxylic acid and 116 mg (0.35 mmol) of [2-(3,4-dichloro-phenyl)-ethyl]-(5-methyl-benzofuran-2-ylmethyl)-amine. MS (ISP) 511.4 (M+H)$^+$.

EXAMPLE 6

Preparation of 5-chloro-1H-indole-7-carboxylic acid [2-(3,4-dichloro-phenyl)-ethyl]-(6-methyl-benzofuran-2-ylmethyl)-amide In analogy to example 1, 22 mg (15%) of the title compound were obtained as an off-white foam starting from 54 mg (0.28 mmol) of 5-chloro-1H-indole-7-carboxylic acid and 92 mg (0.28 mmol) of [2-(3,4-dichloro-phenyl)-ethyl]-(6-methyl-benzofuran-2-ylmethyl)-amine. MS (ISP) 511.4 (M+H)$^+$.

EXAMPLE 7

Preparation of 5-chloro-1H-indole-7-carboxylic acid [2-(3,4-dichloro-phenyl)-ethyl]-(5-methyl-benzo[b]thiophen-2-ylmethyl)-amide In analogy to example 1, 53 mg (46%) of the title compound were obtained as a white foam starting from 42 mg (0.22 mmol) of 5-chloro-1H-indole-7-carboxylic acid and 76 mg (0.22 mmol) of [2-(3,4-dichloro-phenyl)-ethyl]-(5-methyl-benzo[b]thiophen-2-ylmethyl)-amine. $^1H$NMR (CDCl$_3$, 300 MHz): δ 2.47 (s, 3H), 2.89 (t, J=7.1 Hz, 2H), 3.77 (t, J=7.1 Hz, 2H), 4.93 (s, 2H), 6.51 (dd, J=2.1 and 3.2 Hz, 1H), 6.88 (very br s, 1H), 7.11-7.29 (m, 6H), 7.54 (s, 1H), 7.68 (s, 1H), 7.69 (d, J=7.7 Hz, 1H), 8.79 (br s, 1H).

EXAMPLE 8

Preparation of 5-chloro-1H-indole-7-carboxylic acid [2-(3,4-dichloro-phenyl)-ethyl]-(5-ethyl-benzofuran-2-ylmethyl)-amide In analogy to example 1, 77 mg (63%) of the title compound were obtained as a colorless foam starting from 45 mg (0.23 mmol) of 5-chloro-1H-indole-7-carboxylic acid and 81 mg (0.23 mmol) of [2-(3,4-dichloro-phenyl)-ethyl]-(5-ethyl-benzofuran-2-ylmethyl)-amine. MS (ISP) 525.3 (M+H)$^+$.

EXAMPLE 9

Preparation of 5-chloro-1H-indole-7-carboxylic acid [2-(3,4-dichloro-phenyl)-ethyl]-(5,6-dimethyl-benzofuran-2-ylmethyl)-amide In analogy to example 1, 73 mg (65%) of the title compound were obtained as a colorless foam starting from 42 mg (0.21 mmol) of 5-chloro-1H-indole-7-carboxylic acid and 74 mg (0.21 mmol) of [2-(3,4-dichloro-phenyl)-ethyl]-(5,6-dimethyl-benzofuran-2-ylmethyl)-amine. MS (ISP) 525.2 (M+H)$^+$.

EXAMPLE 10

Preparation of 5-chloro-1H-indole-7-carboxylic acid [2-(3,4-dichloro-phenyl)-ethyl]-(6-ethyl-benzofuran-2-ylmethyl)-amide In analogy to example 1, 23 mg (26%) of the title compound were obtained as a light yellow oil starting from 33 mg (0.17 mmol) of 5-chloro-1H-indole-7-carboxylic acid and 59 mg (0.17 mmol) of [2-(3,4-dichloro-phenyl)-ethyl]-(6-ethyl-benzofuran-2-ylmethyl)-amine. MS (ISP) 525.2 (M+H)$^+$.

EXAMPLE 11

Preparation of 5-chloro-1H-indole-7-carboxylic acid [2-(3,4-dichloro-phenyl)-ethyl]-(5-propyl-benzofuran-2-ylmethyl)-amide In analogy to example 1, 63 mg (63%) of the title compound were obtained as a colorless foam starting from 36 mg (0.19 mmol) of 5-chloro-1H-indole-7-carboxylic acid and 67 mg (0.19 mmol) of [2-(3,4-dichloro-phenyl)-ethyl]-(5-propyl-benzofuran-2-ylmethyl)-amine. MS (ISP) 539.3 (M+H)$^+$.

EXAMPLE 12

Preparation of 5-chloro-1H-indole-7-carboxylic acid (6-chloro-benzo[b]thiophen-2-ylmethyl)-[2-(3,4-dichloro-phenyl)-ethyl]-amide In analogy to example 1, 57 mg (74%) of the title compound were obtained as colorless solid starting from 27 mg (0.14 mmol) of 5-chloro-1H-indole-7-carboxylic acid and 52 mg (0.14 mmol) of (6-chloro-benzo[b]thiophen-2-ylmethyl)-[2-(3,4-dichloro-phenyl)-ethyl]-amine. MS (ISP) 547.2 (M+H)$^+$.

EXAMPLE 13

Preparation of 5-chloro-1H-indole-7-carboxylic acid [2-(3,4-dichloro-phenyl)-ethyl]-(6-trifluoromethyl-benzofuran-2-ylmethyl)-amide In analogy to example 1, 39 mg (63%) of the title compound were obtained as a colorless solid starting from 32 mg (0.16 mmol) of 5-chloro-1H-indole-7-carboxylic acid and 63 mg (0.16 mmol) of [2-(3,4-dichloro-phenyl)-ethyl]-(6-trifluoromethyl-benzofuran-2-ylmethyl)-amine. MS (ISP) 565.2 (M+H)$^+$.

EXAMPLE 14

Preparation of 5-chloro-1H-indole-7-carboxylic acid (5-chloro-benzo[b]thiophen-2-ylmethyl)-[2-(3,4-dichloro-phenyl)-ethyl]-amide In analogy to example 1, 27 mg (61%) of the title compound were obtained as a colorless solid starting from 16 mg (0.08 mmol) of 5-chloro-1H-indole-7-carboxylic acid and 37 mg (0.08 mmol) of (5-chloro-benzo[b]thiophen-2-ylmethyl)-[2-(3,4-dichloro-phenyl)-ethyl]-amine. MS (ISP) 547.2 (M+H)$^+$.

EXAMPLE 15

Preparation of 5-chloro-1H-indole-7-carboxylic acid [2-(3,4-dichloro-phenyl)-ethyl]-(6-methyl-4,5,6,7-tetrahydro-benzo[b]thiophen-2-ylmethyl)-amide In analogy to example 1, 35 mg (47%) of the title compound were obtained as a colorless viscous oil starting from 28 mg (0.14 mmol) of 5-chloro-1H-indole-7-carboxylic acid and 50 mg (0.14 mmol) of [2-(3,4-dichloro-phenyl)-ethyl]-(6-methyl-4,5,6,7-tetrahydro-benzo [b]thiophen-2-ylmethyl)-amine. MS (ISP) 530.9 (M+H)$^+$.

EXAMPLE 16

Preparation of 5-chloro-1H-indole-7-carboxylic acid [2-(3,4-dichloro-phenyl)-ethyl]-(6-trifluoromethyl-4,5,6,7-tetrahydro-benzo[b]thiophen-2-ylmethyl)-amide In analogy to example 1, 35 mg (49%) of the title compound were obtained as a brown viscous oil starting from 24 mg (0.12 mmol) of 5-chloro-1H-indole-7-carboxylic acid and 50 mg (0.12 mmol) of [2-(3,4-dichloro-phenyl)-ethyl]-(6-trifluoromethyl-4,5,6,7-tetrahydro-benzo[b]thiophen-2-ylmethyl)-amine. MS (ISP) 584.9 (M+H)$^+$.

EXAMPLE 17

Preparation of 5-chloro-1H-indole-7-carboxylic acid [2-(3,4-dichloro-phenyl)-ethyl]-(5-methyl-4,5,6,7-tetrahydro-benzo[b]thiophen-2-ylmethyl)-amide In analogy to example 1, 28 mg (37%) of the title compound were obtained as an off-white solid starting from 28 mg (0.14 mmol) of 5-chloro-1H-indole-7-carboxylic acid and 50 mg (0.14 mmol) of [2-(3,4-dichloro-phenyl)-ethyl]-(5-methyl-4,5,6,7-tetrahydro-benzo[b]-thiophen-2-ylmethyl)-amine. MS (ISP) 530.9 (M+H)$^+$.

EXAMPLE 18

Preparation of 5-chloro-1H-indole-7-carboxylic acid [2-(3,4-dichloro-phenyl)-ethyl]-(5-ethyl-4,5,6,7-tetrahydro-benzo[b]thiophen-2-ylmethyl)-amide In analogy to example 1, 26 mg (35%) of the title compound were obtained as a colorless viscous oil starting from 27 mg (0.14 mmol) of 5-chloro-1H-indole-7-carboxylic acid and 50 mg (0.14 mmol) of [2-(3,4-dichloro-phenyl)-ethyl]-(5-ethyl-4,5,6,7-tetrahydro-benzo[b]thiophen-2-ylmethyl)-amine. MS (ISP) 545.1 (M+H)$^+$.

EXAMPLE 19

Preparation of 5-chloro-1H-indole-7-carboxylic acid [2-(3,4-dichloro-phenyl)-ethyl]-(5,5-dimethyl-4,5,6,7-tetrahydro-benzo[b]thiophen-2-ylmethyl)-amide In analogy to example 1, 19 mg (26%) of the title compound were obtained as a colorless viscous oil starting from 27 mg (0.14 mmol) of 5-chloro-1H-indole-7-carboxylic acid and 50 mg (0.14 mmol) of [2-(3,4-dichloro-phenyl)-ethyl]-(5,5-dimethyl-4,5,6,7-tetrahydro-benzo[b]thiophen-2-ylmethyl)-amine. MS (ISP) 545.1 (M+H)$^+$.

EXAMPLE 20

Preparation of 5-chloro-1H-indole-7-carboxylic acid [2-(3,4-dichloro-phenyl)-ethyl]-(6-ethyl-4,5,6,7-tetrahydro-benzo[b]thiophen-2-ylmethyl)-amide In analogy to example 1, 87 mg (59%) of the title compound were obtained as a pink gum starting from 53 mg (0.27 mmol) of 5-chloro-1H-indole-7-carboxylic acid and 100 mg (0.27 mmol) of [2-(3,4-dichloro-phenyl)-ethyl]-(6-ethyl-4,5,6,7-tetrahydro-benzo[b]thiophen-2-ylmethyl)-amine. MS (ISP) 545.1 (M+H)$^+$.

EXAMPLE 21

Preparation of 5-chloro-1H-indole-7-carboxylic acid [2-(3,4-dichloro-phenyl)-ethyl]-(6,6-dimethyl-4,5,6,7-tetrahydro-benzo[b]thiophen-2-ylmethyl)-amide In analogy to example 1, 39 mg (23%) of the title compound were obtained as a colorless gum starting from 53 mg (0.27 mmol) of 5-chloro-1H-indole-7-carboxylic acid and 100 mg (0.27 mmol) of [2-(3,4-dichloro-phenyl)-ethyl]-(6,6-dimethyl-4,5,6,7-tetrahydro-benzo[b]thiophen-2-ylmethyl)-amine. MS (ISP) 545.1 (M+H)$^+$.

EXAMPLE 22

Preparation of 5-chloro-N-[2-(3,4-dichloro-phenyl)-ethyl]-N-(5,5-dimethyl-4,5,6,7-tetrahydro-benzo[b]thiophen-2-ylmethyl)-2-ethylamino-benzamide In analogy to example 1, 31 mg (38%) of the title compound were obtained as a light yellow oil starting from 29 mg (0.15 mmol) of 5-chloro-2-ethylamino-benzoic acid and 54 mg (0.15 mmol) of [2-(3,4-dichloro-phenyl)-ethyl]-(5,5-dimethyl-4,5,6,7-tetrahydro-benzo[b]thiophen-2-ylmethyl)-amine. MS (ISP) 549.0 (M+H)$^+$.

EXAMPLE 23

Preparation of 5-chloro-N-[2-(3,4-dichloro-phenyl)-ethyl]-N-(5,5-dimethyl-4,5,6,7-tetrahydro-benzo[b]thiophen-2-ylmethyl)-2-methylamino-nicotinamide In analogy to example 1, 42 mg (53%) of the title compound were obtained as a light yellow oil starting from 27 mg (0.15 mmol) of 5-chloro-2-methylamino-nicotinic acid (synthesized according to WO9530676) and 54 mg (0.15 mmol) of [2-(3,4-dichloro-phenyl)-ethyl]-(5,5-dimethyl-4,5,6,7-tetrahydro-benzo[b]thiophen-2-ylmethyl)-amine. MS (ISP) 535.9 (M+H)$^+$.

EXAMPLE 24

Preparation of 5-chloro-2-cyclopropylamino-N-[2-(3,4-dichloro-phenyl)-ethyl]-N-(6-ethyl-4,5,6,7-tetrahydro-benzo[b]thiophen-2-ylmethyl)-benzamide In analogy to example 1, 68 mg (53%) of the title compound were obtained as a colorless gum starting from 48 mg (0.23 mmol) of 5-chloro-2-cyclopropylamino-benzoic acid and 83 mg (0.23 mmol) of [2-(3,4-dichloro-phenyl)-ethyl]-

(6-ethyl-4,5,6,7-tetrahydro-benzo[b]thiophen-2-ylmethyl)-amine. MS (ISP) 561.2 (M+H)$^+$.

EXAMPLE 25

Preparation of 5-chloro-1H-indole-7-carboxylic acid (6,6-dimethyl-4,5,6,7-tetrahydro-benzo[b]thiophen-2-ylmethyl)-[2-(4-fluoro-phenyl)-ethyl]-amide In analogy to example 1, 67 mg (61%) the title compound were obtained as a pink solid starting from 47 mg (0.24 mmol) of 5-chloro-1H-indole-7-carboxylic acid and 70 mg (0.22 mmol) of (6,6-dimethyl-4,5,6,7-tetrahydro-benzo[b]thiophen-2-ylmethyl)-[2-(4-fluoro-phenyl)-ethyl]-amine. MS (ISP) 495.1 (M+H)$^+$.

EXAMPLE 26

Preparation of 5-chloro-N-(6,6-dimethyl-4,5,6,7-tetrahydro-benzo[b]thiophen-2-ylmethyl)-N-[2-(4-fluoro-phenyl)-ethyl]-2-methylamino-nicotinamide In analogy to example 1, 73 mg (68%) of the title compound were obtained as a colorless gum starting from 45 mg (0.24 mmol) of 5-chloro-2-methylamino-nicotinic acid and 70 mg (0.22 mmol) of (6,6-dimethyl-4,5,6,7-tetrahydro-benzo[b]thiophen-2-ylmethyl)-[2-(4-fluoro-phenyl)-ethyl]-amine. MS (ISP) 486.2 (M+H)$^+$.

EXAMPLE 27

Preparation of 5-chloro-1H-indole-7-carboxylic acid (6,6-dimethyl-4,5,6,7-tetrahydro-benzo[b]thiophen-2-ylmethyl)-[2-(3-trifluoromethyl-phenyl)-ethyl]-amide In analogy to example 1, 73 mg (68%) of the title compound were obtained as a colorless gum starting from 47 mg (0.24 mmol) of 5-chloro-1H-indole-7-carboxylic acid and 80 mg (0.22 mmol) of (6,6-dimethyl-4,5,6,7-tetrahydro-benzo[b]thiophen-2-ylmethyl)-[2-(3-trifluoromethyl-phenyl)-ethyl]-amine. MS (ISP) 545.1 (M+H)$^+$.

EXAMPLE 28

Preparation of 5-chloro-N-(6,6-dimethyl-4,5,6,7-tetrahydro-benzo[b]thiophen-2-ylmethyl)-2-methylamino-N-[2-(3-trifluoromethyl-phenyl)-ethyl]-nicotinamide In analogy to example 1, 84 mg (72%) of the title compound were obtained as a colorless gum starting from 45 mg (0.24 mmol) of 5-chloro-2-methylamino-nicotinic acid and 80 mg (0.22 mmol) of (6,6-dimethyl-4,5,6,7-tetrahydro-benzo[b]thiophen-2-ylmethyl)-[2-(3-trifluoromethyl-phenyl)-ethyl]-amine. MS (ISP) 536.1 (M+H)$^+$.

EXAMPLE 29

Preparation of 5-chloro-1H-indole-7-carboxylic acid [2-(3,4-dichloro-phenyl)-ethyl]-(6,6-dimethyl-4,5,6,7-tetrahydro-benzothiazol-2-ylmethyl)-amide In analogy to example 1, 6 mg (18%) of the title compound were obtained as a yellow oil starting from 13 mg (0.07 mmol) of 5-chloro-1H-indole-7-carboxylic acid and 23 mg (0.06 mmol) of [2-(3,4-dichloro-phenyl)-ethyl]-(6,6-dimethyl-4,5,6,7-tetrahydro-benzothiazol-2-ylmethyl)-amine. MS (ISP) 546.0 (M+H)$^+$.

EXAMPLE 30

Preparation of 5-chloro-1H-indole-7-carboxylic acid (5,5-dimethyl-4,5,6,7-tetrahydro-benzo[b]thiophen-2-ylmethyl)-[2-(4-fluoro-phenyl)-ethyl]-amide In analogy to example 1, 81 mg (65%) of the title compound were obtained as a viscous pink oil starting from 54 mg (0.28 mmol) of 5-chloro-1H-indole-7-carboxylic acid and 80 mg (0.25 mmol) of (5,5-dimethyl-4,5,6,7-tetrahydro-benzo[b]thiophen-2-ylmethyl)-[2-(4-fluoro-phenyl)-ethyl]-amine. MS (ISP) 495.4 (M+H)$^+$.

EXAMPLE 31

Preparation of 5-chloro-N-(5,5-dimethyl-4,5,6,7-tetrahydro-benzo[b]thiophen-2-ylmethyl)-N-[2-(4-fluoro-phenyl)-ethyl]-2-methylamino-nicotinamide In analogy to example 1, 110 mg (90%) of the title compound were obtained as a viscous yellow oil starting from 47 mg (0.25 mmol) of 5-chloro-2-methylamino-nicotinic acid and 80 mg (0.25 mmol) of (5,5-dimethyl-4,5,6,7-tetrahydro-benzo[b]thiophen-2-ylmethyl)-[2-(4-fluoro-phenyl)-ethyl]-amine. MS (ISP) 486.4 (M+H)$^+$.

EXAMPLE 32

Preparation of 5-chloro-1H-indole-7-carboxylic acid (5,5-dimethyl-4,5,6,7-tetrahydro-benzo[b]thiophen-2-ylmethyl)-[2-(3-trifluoromethyl-phenyl)-ethyl]-amide In analogy to example 1, 66 mg (56%) of the title compound were obtained as a colorless gum starting from 47 mg (0.24 mmol) of 5-chloro-1H-indole-7-carboxylic acid and 80 mg (0.22 mmol) of (5,5-dimethyl-4,5,6,7-tetrahydro-benzo[b]thiophen-2-ylmethyl)-[2-(3-trifluoromethyl-phenyl)-ethyl]-amine. MS (ISP) 545.4 (M+H)$^+$.

EXAMPLE 33

Preparation of 5-chloro-N-(5,5-dimethyl-4,5,6,7-tetrahydro-benzo[b]thiophen-2-ylmethyl)-2-methylamino-N-[2-(3-trifluoromethyl-phenyl)-ethyl]-nicotinamide In analogy to example 1, 67 mg (57%) of the title compound were obtained as a yellow gum starting from 41 mg (0.22 mmol) of 5-chloro-2-methylamino-nicotinic acid and 80 mg (0.22 mmol) of (5,5-dimethyl-4,5,6,7-tetrahydro-benzo[b]thiophen-2-ylmethyl)-[2-(3-trifluoromethyl-phenyl)-ethyl]-amine. MS (ISP) 536.3 (M+H)$^+$.

EXAMPLE 34

Preparation of 5-chloro-6-fluoro-1H-indole-7-carboxylic acid (5,5-dimethyl-4,5,6,7-tetrahydro-benzo[b]thiophen-2-ylmethyl)-[2-(4-fluoro-phenyl)-ethyl]-amide In analogy to example 1, 78 mg (48%) of the title compound were obtained as an orange gum starting from 67 mg (0.32 mmol) of 5-chloro-6-fluoro-1H-indole-7-carboxylic acid and 100 mg (0.32 mmol) of (5,5-dimethyl-4,5,6,7-tetrahydro-benzo[b]thiophen-2-ylmethyl)-[2-(4-fluoro-phenyl)-ethyl]-amine. MS (ISP) 513.4 (M+H)$^+$.

EXAMPLE 35

Preparation of 5-chloro-6-fluoro-1H-indole-7-carboxylic acid (5,5-dimethyl-4,5,6,7-tetrahydro-benzo[b]thiophen-2-ylmethyl)-[2-(3-trifluoromethyl-phenyl)-ethyl]-amide In analogy to example 1, 87 mg (57%) of the title compound were obtained as a yellow gum starting from 58 mg (0.27 mmol) of 5-chloro-6-fluoro-1H-indole-7-carboxylic acid and 100 mg (0.27 mmol) of (5,5-dimethyl-4,5,6,7-tetrahydro-benzo[b]thiophen-2-ylmethyl)-[2-(3-trifluoromethyl-phenyl)-ethyl]-amine. MS (ISP) 563.4 (M+H)$^+$.

EXAMPLE 36

Preparation of 5-chloro-6-fluoro-1H-indole-7-carboxylic acid [2-(3,4-dichloro-phenyl)-ethyl]-(5,5-dimethyl-4,5,6,7-tetrahydro-benzo[b]thiophen-2-ylmethyl)-amide In analogy to example 1, 72 mg (47%) of the title compound were obtained as an orange gum starting from 58 mg (0.27 mmol) of 5-chloro-6-fluoro-1H-indole-7-carboxylic acid and 100 mg (0.27 mmol) of [2-(3,4-dichloro-phenyl)-ethyl]-(5,5-dimethyl-4,5,6,7-tetrahydro-benzo[b]thiophen-2-ylmethyl)-amine. MS (ISP) 563.4 (M+H)$^+$.

EXAMPLE 37

Preparation of N-(6-tert-butyl-pyridin-3-ylmethyl)-5-chloro-N-[2-(3,4-dichloro-phenyl)-ethyl]-2-methylamino-nicotinamide In analogy to example 1, the title compound was obtained from 5-chloro-2-methylamino-nicotinic acid and (6-tert-butyl-pyridin-3-ylmethyl)-[2-(3,4-dichloro-phenyl)-ethyl]-amine. Light yellow gum, MS (ISP) 505.3 (M+H)$^+$.

EXAMPLE 38

Preparation of N-(6-tert-butyl-pyridin-3-ylmethyl)-2-chloro-N-[2-(3,4-dichloro-phenyl)-ethyl]-5-methylamino-isonicotinamide In analogy to example 1, the title compound was obtained from 2-chloro-5-methylamino-isonicotinic acid and (6-tert-butyl-pyridin-3-ylmethyl)-[2-(3,4-dichloro-phenyl)-ethyl]-amine. Light yellow gum, MS (ISP) 505.3 (M+H)$^+$.

EXAMPLE 39

Preparation of N-(5-tert-butyl-pyridin-2-ylmethyl)-5-chloro-N-[2-(3,4-dichloro-phenyl)-ethyl]-2-methylamino-nicotinamide In analogy to example 1, the title compound was obtained from 5-chloro-2-methylamino-nicotinic acid and (5-tert-butyl-pyridin-2-ylmethyl)-[2-(3,4-dichloro-phenyl)-ethyl]-amine. Yellow oil, MS (ISP) 505.0 (M+H)$^+$.

EXAMPLE 40

Preparation of N-(5-tert-butyl-pyridin-2-ylmethyl)-5-chloro-N-[2-(3,4-dichloro-phenyl)-ethyl]-2-methylamino-benzamide In analogy to example 1, the title compound was obtained from 5-chloro-2-(methyl-amino)benzoic acid (synthesized according to *J. Heterocycl. Chem.* 1979, 16, 661) and (5-tert-butyl-pyridin-2-ylmethyl)-[2-(3,4-dichloro-phenyl)-ethyl]-amine. Light yellow oil, MS (ISP) 506.0 (M+H)$^+$.

EXAMPLE 41

Preparation of N-(6-tert-butyl-pyridin-3-ylmethyl)-5-chloro-N-[2-(3,4-dichloro-phenyl)-ethyl]-2-methylamino-benzamide In analogy to example 1, the title compound was obtained from 5-chloro-2-(methyl-amino)benzoic acid and (6-tert-butyl-pyridin-3-ylmethyl)-[2-(3,4-dichloro-phenyl)-ethyl]-amine. Light yellow oil, MS (ISP) 504.3 (M+H)$^+$.

EXAMPLE 42

Preparation of 5-chloro-6-fluoro-1H-indole-7-carboxylic acid (6-tert-butyl-pyridin-3-ylmethyl)-[2-(3,4-dichloro-phenyl)-ethyl]-amide In analogy to example 1, the title compound was obtained from 5-chloro-6-fluoro-1H-indole-7-carboxylic acid and (6-tert-butyl-pyridin-3-ylmethyl)-[2-(3,4-dichloro-phenyl)-ethyl]-amine. Off-white solid, MS (ISP) 532.1 (M+H)$^+$.

EXAMPLE 43

Preparation of N-(6-tert-butyl-pyridin-3-ylmethyl)-5-chloro-2-methylamino-N-[2-(3-trifluoromethyl-phenyl)-ethyl]-nicotinamide In analogy to example 1, the title compound was obtained from 5-chloro-2-methylamino-nicotinic acid and (6-tert-butyl-pyridin-3-ylmethyl)-[2-(3-trifluoromethyl-phenyl)-ethyl]-amine. Light yellow gum, MS (ISP) 505.5 (M+H)$^+$.

EXAMPLE 44

Preparation of N-(6-tert-butyl-pyridin-3-ylmethyl)-5-chloro-2-methylamino-N-[2-(3-trifluoromethyl-phenyl)-ethyl]-benzamide In analogy to example 1, the title compound was obtained from 5-chloro-2-(methyl-amino)benzoic acid and (6-tert-butyl-pyridin-3-ylmethyl)-[2-(3-trifluoromethyl-phenyl)-ethyl]-amine. Light yellow gum, MS (ISP) 504.3 (M+H)$^+$.

EXAMPLE 45

Preparation of 5-chloro-6-fluoro-1H-indole-7-carboxylic acid (6-tert-butyl-pyridin-3-ylmethyl)-[2-(3-trifluoromethyl-phenyl)-ethyl]-amide In analogy to example 1, the title compound was obtained from 5-chloro-6-fluoro-1H-indole-7-carboxylic acid and (6-tert-butyl-pyridin-3-ylmethyl)-[2-(3-trifluoromethyl-phenyl)-ethyl]-amine. Light yellow gum, MS (ISP) 532.3 (M+H)$^+$.

EXAMPLE 46

Preparation of N-(5-tert-butyl-pyridin-2-ylmethyl)-5-chloro-2-methylamino-N-[2-(3-trifluoromethyl-phenyl)-ethyl]-nicotinamide In analogy to example 1, the title compound was obtained from 5-chloro-2-methylamino-nicotinic acid and (5-tert-butyl-pyridin-2-ylmethyl)-[2-(3-trifluoromethyl-phenyl)-ethyl]-amine. Light yellow gum, MS (ISP) 505.4 (M+H)$^+$.

EXAMPLE 47

Preparation of N-(5-tert-butyl-pyridin-2-ylmethyl)-5-chloro-2-methylamino-N-[2-(3-trifluoromethyl-phenyl)-ethyl]-benzamide In analogy to example 1, the title compound was obtained from 5-chloro-2-(methyl-amino)benzoic acid and (5-tert-butyl-pyridin-2-ylmethyl)-[2-(3-trifluoromethyl-phenyl)-ethyl]-amine. Light yellow solid, MS (ISP) 504.4 (M+H)$^+$.

EXAMPLE 48

Preparation of 5-chloro-6-fluoro-1H-indole-7-carboxylic acid (5-tert-butyl-pyridin-2-ylmethyl)-[2-(3-trifluoromethyl-phenyl)-ethyl]-amide In analogy to example 1, the title compound was obtained from 5-chloro-6-fluoro-1H-indole-7-carboxylic acid and (5-tert-butyl-pyridin-2-ylmethyl)-[2-(3-trifluoromethyl-phenyl)-ethyl]-amine. Light brown foam, MS (ISP) 532.3 (M+H)$^+$.

EXAMPLE 49

Preparation of N-(6-tert-butyl-pyridin-3-ylmethyl)-5-chloro-N-[2-(4-chloro-phenyl)-ethyl]-2-methylamino-benzamide In analogy to example 1, the title compound was obtained from 5-chloro-2-(methyl-amino)benzoic acid and (6-tert-butyl-pyridin-3-ylmethyl)-[2-(4-chloro-phenyl)-ethyl]-amine. Light yellow gum, MS (ISP) 470.5 (M+H)$^+$.

EXAMPLE 50

Preparation of 5-chloro-6-fluoro-1H-indole-7-carboxylic acid (6-tert-butyl-pyridin-3-ylmethyl)-[2-(4-chloro-phenyl)-ethyl]-amide In analogy to example 1, the title compound was obtained from 5-chloro-6-fluoro-1H-indole-7-carboxylic acid and (6-tert-butyl-pyridin-3-ylmethyl)-[2-(4-chloro-phenyl)-ethyl]-amine. White foam, MS (ISP) 498.4 (M+H)$^+$.

EXAMPLE 51

Preparation of 5-chloro-6-fluoro-1H-indole-7-carboxylic acid (5-tert-butyl-thiophen-2-ylmethyl)-[2-(3-trifluoromethyl-phenyl)-ethyl]-amide In analogy to example 1, 46 mg (51%) of the title compound were obtained as a light yellow viscous oil starting from 36 mg (0.17 mmol) of 5-chloro-6-fluoro-1H-indole-7-carboxylic acid and 58 mg (0.17 mmol) of (5-tert-butyl-thiophen-2-ylmethyl)-[2-(3-trifluoromethyl-phenyl)-ethyl]-amine. MS (ISP) 537.4 (M+H)$^+$.

EXAMPLE 52

Preparation of N-(5-tert-butyl-thiophen-2-ylmethyl)-5-chloro-2-methylamino-N-[2-(3-trifluoromethyl-phenyl)-ethyl]-benzamide In analogy to example 1, 57 mg (67%) of the title compound were obtained as a light yellow viscous oil starting from 31 mg (0.17 mmol) of 5-chloro-2-(methylamino)benzoic acid and 57 mg (0.17 mmol) of (5-tert-butyl-thiophen-2-ylmethyl)-[2-(3-trifluoromethyl-phenyl)-ethyl]-amine. MS (ISP) 509.5 (M+H)$^+$.

EXAMPLE 53

Preparation of N-(5-tert-butyl-thiophen-2-ylmethyl)-5-chloro-2-methylamino-N-[2-(3-trifluoromethyl-phenyl)-ethyl]-nicotinamide In analogy to example 1, 65 mg (85%) of the title compound were obtained as a light yellow viscous oil starting from 28 mg (0.15 mmol) of 5-chloro-2-methylamino-nicotinic acid and 51 mg (0.15 mmol) of (5-tert-butyl-thiophen-2-ylmethyl)-[2-(3-trifluoromethyl-phenyl)-ethyl]-amine. MS (ISP) 510.5 (M+H)$^+$.

EXAMPLE 54

Preparation of N-(4-tert-butyl-thiazol-2-ylmethyl)-5-chloro-2-methylamino-N-[2-(3-trifluoromethyl-phenyl)-ethyl]-benzamide In analogy to example 1, 58 mg (35%) of the title compound were obtained as a viscous yellow oil starting from 42 mg (0.22 mmol) of 5-chloro-2-(methylamino)-benzoic acid and 80 mg (0.22 mmol) of (4-tert-butyl-thiazol-2-ylmethyl)-[2-(3-trifluoromethyl-phenyl)-ethyl]-amine. MS (ISP) 510.5 (M+H)$^+$.

EXAMPLE 55

Preparation of N-(4-tert-butyl-thiazol-2-ylmethyl)-5-chloro-N-[2-(4-chloro-phenyl)-ethyl]-2-methylamino-benzamide In analogy to example 1, 45 mg (27%) of the title compound were obtained as a viscous yellow oil starting from 45 mg (0.24 mmol) of 5-chloro-2-(methylamino)-benzoic acid and 80 mg (0.24 mmol) of (4-tert-butyl-thiazol-2-ylmethyl)-[2-(4-chloro-phenyl)-ethyl]-amine. MS (ISP) 476.2 (M+H)$^+$.

EXAMPLE 56

Preparation of 5-chloro-6-fluoro-1H-indole-7-carboxylic acid (4-tert-butyl-thiazol-2-ylmethyl)-[2-(3-trifluoromethyl-phenyl)-ethyl]-amide In analogy to example 1, 54 mg (31%) of the title compound were obtained as a viscous yellow oil starting from 48 mg (0.22 mmol) of -chloro-6-fluoro-1H-indole-7-carboxylic acid and 80 mg (0.22 mmol) of (4-tert-butyl-thiazol-2-ylmethyl)-[2-(3-trifluoromethyl-phenyl)-ethyl]-amine. MS (ISP) 538.2 (M+H)$^+$.

Compounds of formula II are commercially available or may be prepared applying known techniques.

Compounds of formula III are commercially available or may be prepared applying known techniques.

EXAMPLE S1

Preparation of benzofuran-2-ylmethyl-[2-(3,4-dichloro-phenyl)-ethyl]-amine

A solution of 150 mg (1.03 mmol) of benzofuran-2-carbaldehyde and 195 mg (1.03 mmol) of 2-(3,4-dichloro-phenyl)-ethylamine in methanol (4 ml) was heated to reflux for 3 h. Then the reaction mixture was allowed to cool to RT and 58 mg (1.54 mmol) of sodium borohydride were added. The mixture was heated to reflux over night. After cooling to RT, 0.1 N sodium hydroxide solution was added and the mixture was extracted with ethyl acetate. The combined organic extracts were washed with brine, dried ($MgSO_4$) and concentrated. The residue was purified by column chromatography (silica gel; dichloromethane and dichloromethane/methanol 95:5). The title compound was isolated as yellow oil (249 mg, 76%). MS (ISP) 320.2 $(M+H)^+$.

EXAMPLE S2

Preparation of 5-chloro-1H-indole-7-carboxylic acid 8.26 g (40 mmol) of 2-bromo-4-chloro-aniline were added dropwise at 0° C. to 44 ml (44 mmol) of a 1M solution of boron trichloride in dichloromethane under nitrogen. After complete addition 25 ml of 1,2-dichloroethane were added. After stirring for 30 min at RT 3 ml (48 mmol) of chloroacetonitrile, 5.9 g (44 mmol) of aluminium trichloride and 55 ml 1,2-dichloroethane were added. At 75° C. dichloromethane was distilled off and the reaction mixture was heated to reflux over night. After cooling to RT 80 ml of 2N aqueous solution of HCl was added dropwise and the reaction mixture was heated to 80° C. for 1 hour. The reaction mixture was then cooled to RT and filtered. The solid was washed with dichloromethane. The combined organic layers were washed with water and saturated aqueous NaCl solution, dried over sodium sulfate, filtered and the solvent was evaporated to yield a mixture of starting material and of 1-(2-amino-3-bromo-5-chloro-phenyl)-2-chloro-ethanone.

The crude mixture obtained in step a) was dissolved in 90% aqueous dioxane and 750 mg (20 mmol) of sodium borohydride were added in portions. The reaction mixture was heated to reflux overnight. The solvent was evaporated, the residue dissolved in dichloromethane. The organic layer was washed once with 1N aqueous HCl solution, once with saturated aqueous $NaHCO_3$ solution and once with saturated aqueous sodium chloride solution, dried over sodium sulfate, filtered and the solvent was evaporated. The residue was purified by column chromatography (100 g silica gel, heptane/dichloromethane 4:1) to yield 3.37 g (37%) of 7-bromo-5-chloro-1H-indole as yellow crystals. MS (EI) 229.0 (80), 230.9 (100), 233.0 (25) $(M)^+$.

1.15 g (5 mmol) of 7-bromo-5-chloro-1H-indole were dissolved in 30 ml THF. At −75° C. under argon 9.4 ml (15 mmol) of a 1.6 M n-butyllithium solution in hexane were added dropwise. After complete addition the reaction mixture was stirred at 5° C. for 30 min, cooled to −75° C. and 10 g dry ice was added. The reaction mixture was warmed to RT and stirred for 15 min. It was poured onto 100 ml of water and extracted twice with ethyl acetate. The aqueous layer was acidified with 1N aqueous HCl solution and extracted twice with dichloromethane. The combined organic layers were dried over sodium sulfate, filtered and the solvent was evaporated. The residue was treated with hexane and stirred for 10 min. The precipitate was filtered, washed with hexane and dried to yield 700 mg (72%) of 5-chloro-1H-indole-7-carboxylic acid as a white solid. MS (ISP) 194.0 $(M-H)^-$.

EXAMPLE S3

Preparation of benzo[b]thiophen-2-ylmethyl-[2-(3,4-dichloro-phenyl)-ethyl]-amine To a solution of 300 mg (1.68 mmol) of benzo[b]thiophene-2-carboxylic acid in DMF (8 ml) were added 320 mg (1.68 mmol) of 2-(3,4-dichloro-phenyl)-ethylamine and 595 mg (1.85 mmol) of TBTU. After 10 min 1.47 ml (8.42 mmol) of N,N-diisopropylethyl amine were added and the reaction mixture was stirred over night at RT. Then water was added and the mixture was extracted with ethyl acetate. The combined organic extracts were washed with water, brine, sat. $NaHCO_3$ solution, 1N HCl and again with brine. The organic layer was then dried ($MgSO_4$) and concentrated. The remaining residue was purified by column chromatography (silica gel; ethyl acetate/cyclohexane 9:1) to yield 515 mg (87%) of benzo[b]thiophene-2-carboxylic acid[2-(3,4-dichloro-phenyl)-ethyl]-amide as a white solid. MS (ISP) 350.2 $(M+H)^+$.

A solution of 364 mg (1.04 mmol) of benzo[b]thiophene-2-carboxylic acid[2-(3,4-di-chloro-phenyl)-ethyl]-amide in 10 ml of THF was added dropwise to 5.2 ml of a 1 molar solution of $BH_3$-THF complex in THF at 0° C. The reaction mixture was stirred for 30 min at RT and then heated to reflux over night. Then 2 ml of 6 N HCl were added very carefully at ambient temperature and the mixture was heated again to reflux for 2 hours. After cooling to RT, the pH was adjusted to 8-9 by addition of 1 N sodium hydroxide solution and the mixture was extracted twice with ethyl acetate. The combined organic layers were washed with brine, dried with magnesium sulfate, filtered and concentrated. Final purification of the residue (silica gel; dichloromethane/methanol 95:5) yielded 113 mg (32%) of benzo[b]thiophen-2-ylmethyl-[2-(3,4-dichloro-phenyl)-ethyl]-amine as off-white solid. MS (ISP) 336.2 $(M+H)^+$.

EXAMPLE S4

Preparation of [2-(3,4-dichloro-phenyl)-ethyl]-(6,7-dimethyl-benzofuran-2-ylmethyl)-amine In analogy to example S1) 91 mg (92%) of the title compound were obtained as light yellow oil starting from 49 mg (0.28 mmol) of 6,7-dimethyl-benzofuran-2-carbaldehyde (synthesized according to *J. Org. Chem.* 2000, 43, 2929-2937) and 54 mg (0.28 mmol) of 2-(3,4-dichloro-phenyl)-ethylamine. $^{1H}$NMR ($CDCl_3$, 300 MHz): δ 2.37 (s, 3H), 2.40 (s, 3H), 2.76 (t, J=6.9 Hz, 2H), 2.90 (t, J=6.9 Hz, 2H), 3.92 (s, 2H), 6.46 (s, 1H), 7.01 (m, 2H), 7.22 (d, J=7.9 Hz, 1H), 7.28 (d, J=1.9 Hz, 1H), 7.32 (d, J=8.3 Hz, 1H).

EXAMPLE S5

Preparation of (5,7-dichloro-benzofuran-2-ylmethyl)-[2-(3,4-dichloro-phenyl)-ethyl]-amine In analogy to example S1) 87 mg (93%) of the title compound was obtained as orange oil starting from 51 mg (0.24 mmol) of 5,7-dichloro-benzofuran-2-carbaldehyde (synthesized according to *Eur. J. Org. Chem.* 1996, 31, 449-460) and 45 mg (0.24 mmol) of 2-(3,4-dichloro-phenyl)-ethylamine. $^{1H}$NMR (CDCl$_3$, 300 MHz): δ 2.70 (m, 2H), 2.84 (m, 2H), 3.88 (s, 2H), 6.45 (s, 1H), 695 (m, 1H), 7.14-7.36 (m, 4H).

EXAMPLE S6

Preparation of [2-(3,4-dichloro-phenyl)-ethyl]-(5-methyl-benzofuran-2-ylmethyl)-amine To a solution of 100 mg (0.73 mmol) of 2-hydroxy-5-methyl-benzaldehyde in DMF (1 ml) were added 109 μl (0.92 mmol) of 2-bromo-1,1-dimethoxy-ethane and 112 mg (0.81 mmol) of potassium carbonate. The reaction mixture was heated to reflux for 90 min. Then water was added at RT and the mixture was extracted with ether. The combined organic extracts were washed with brine, dried (MgSO$_4$) and concentrated to yield 2-(2,2-dimethoxy-ethoxy)-5-methyl-benzaldehyde as a yellow oil (154 mg, 93%). $^{1H}$NMR (CDCl$_3$, 300 MHz): δ 2.32 (s, 3H), 3.48 (s, 6H), 4.09 (d, J=5.3 Hz, 2H), 4.75 (t, J=5.3 Hz, 1H), 6.89 (d, J=8.4 Hz, 1H), 7.34 (dd, J=8.4 and 2.3 Hz, 1H), 7.64 (d, J=2.3 Hz, 1H), 10.48 (s, 1H).

154 mg (0.69 mmol) of 2-(2,2-dimethoxy-ethoxy)-5-methyl-benzaldehyde were dissolved in trifluoroacetic acid and the reaction mixture was heated to reflux for 15 min. After cooling to RT ether was added and the mixture was washed with water and 10% aqueous KHCO$_3$ solution. The organic layer was then dried (MgSO$_4$) and concentrated and the residue was purified by column chromatography (silica gel; ethyl acetate/cyclohexane 4:1) to yield 76 mg (48%) of 5-methyl-benzofuran-2-carbaldehyde as brown oil. $^{1H}$NMR (CDCl$_3$, 300 MHz): δ 2.47 (s, 3H), 7.34 (d, J=8.7 Hz, 1H), 7.50 (m, 3H), 9.85 (s, 1H).

In analogy to example S1) 111 mg (0.69 mmol) of 5-methyl-benzofuran-2-carbaldehyde and 144 mg (0.76 mmol) of 2-(3,4-dichloro-phenyl)-ethylamine were reacted to yield 206 mg (89%) of [2-(3,4-dichloro-phenyl)-ethyl]-(5-methyl-benzofuran-2-ylmethyl)-amine as light brown oil. $^{1H}$NMR (CDCl$_3$, 300 MHz): δ 2.42 (s, 3H), 2.77 (t, J=6.7 Hz, 2H), 2.89 (t, J=6.7 Hz, 2H), 3.91 (s, 2H), 6.46 (s, 1H), 7.04 (m, 2H), 7.32 (m, 4H).

EXAMPLE S7

Preparation of [2-(3,4-dichloro-phenyl)-ethyl]-(6-methyl-benzofuran-2-ylmethyl)-amine 109 μl (0.93 mmol) of tin-tetrachloride and 882 μl (3.70 mmol) of tri-n-butylamine were added to a solution of 1.0 g (9.25 mmol) of 3-methyl-phenol in toluene (12 ml) and the mixture was stirred for 30 min at RT. Then 611 g of paraformaldehyde were added and the resulting mixture was heated to 100° C. for 16 hours. After cooling to RT water (40 ml) was added and the pH was adjusted to 2 by addition of 1N HCl. This mixture was extracted with ether. The combined organic extracts were washed with brine, dried (MgSO$_4$) and concentrated. The residue was purified by column chromatography (silica gel; ether/cyclohexane 1:15) to yield 131 mg (10%) of 2-hydroxy-4-methyl-benzaldehyde as colorless crystals. $^{1H}$NMR (CDCl$_3$, 300 MHz): δ 2.38 (s, 3H), 6.80 (s, 1H), 6.82 (d, J=7.9 Hz, 1H), 7.43 (d, J=7.9 Hz, 1H), 9.83 (s, 1H), 11.04 (s, 1H).

In analogy to example S6 (steps a to c) 131 mg (0.96 mmol) of 2-hydroxy-4-methyl-benz-aldehyde were converted into 204 mg (0.49 mmol) of [2-(3,4-dichloro-phenyl)-ethyl]-(6-methyl-benzofuran-2-ylmethyl)-amine. The product was obtained as brown oil. $^{1H}$NMR (CDCl$_3$, 300 MHz): δ 2.46 (s, 3H), 2.77 (m, 2H), 2.89 (m, 2H), 3.91 (s, 2H), 6.48 (s, 1H), 7.04 (m, 2H), 7.32 (m, 5H).

EXAMPLE S8

Preparation of [2-(3,4-dichloro-phenyl)-ethyl]-(5-methyl-benzo[b]thiophen-2-ylmethyl)-amine In analogy to example S1) 76 mg (25%) of the title compound was obtained as yellow oil starting from 150 mg (0.85 mmol) of 5-methyl-benzo[b]thiophene-2-carbaldehyde (*J. Chem. Soc.*(C) 1970, 1013-1016) and 178 mg (0.94 mmol) of 2-(3,4-dichloro-phenyl)-ethylamine. $^{1H}$NMR (CDCl$_3$, 300 MHz): δ 2.44 (s, 3H), 2.75 (t, J=6.9 Hz, 2H), 2.90 (t, J=6.9 Hz, 2H), 4.04 (s, 2H), 7.01 (m, 2H), 7.10 (d, J=8.1 Hz, 1H), 7.29 (s, 1H), 7.32 (d, J=8.3 Hz, 1H), 7.47 (s, 1H), 7.65 (d, J=8.1 Hz, 1H).

EXAMPLE S9

Preparation of [2-(3,4-dichloro-phenyl)-ethyl]-(5-ethyl-benzofuran-2-ylmethyl)-amine In analogy to example S6 (steps a to c) 316 mg (2.11 mmol) of 5-ethyl-2-hydroxy-benz-aldehyde were converted into 240 mg of the title compound. The compound was obtained as a yellow liquid. $^{1H}$NMR (CDCl$_3$, 300 MHz): δ 1.27 (t, J=7.6 Hz, 3H), 2.72 (q, J=7.6 Hz, 2H), 2.77 (m, 2H), 2.90 (m, 2H), 3.92 (s, 2H), 6.48 (s, 1H), 7.02 (dd, J=8.2 and 1.9 Hz, 1H), 7.09 (dd, J=8.4 and 1.7 Hz, 1H), 7.29 (d, J=1.9 Hz, 1H), 7.34 (m, 3H).

EXAMPLE S10

Preparation of [2-(3,4-dichloro-phenyl)-ethyl]-(5,6-dimethyl-benzofuran-2-ylmethyl)-amine In analogy to example S6 (steps a to c) 318 mg (2.12 mmol) of 2-hydroxy-4,5-dimethyl-benzaldehyde were converted into 305 mg of the title compound. The compound was obtained as an orange solid. $^{1H}$NMR (CDCl$_3$, 300 MHz): δ 2.31 (s, 3H), 2.34 (s, 3H), 2.76 (m, 2H), 2.88 (m, 2H), 3.90 (s, 2H), 6.43 (s, 1H), 7.01 (dd, J=8.2 and 2.1 Hz, 1H), 7.21 (s, 1H), 7.26 (s, 1H), 7.27 (d, J=2.1 Hz, 1H), 7.32 (d, J=8.2 Hz, 1H).

EXAMPLE S11

Preparation of [2-(3,4-dichloro-phenyl)-ethyl]-(6-ethyl-benzofuran-2-ylmethyl)-amine In analogy to example S7 (steps a to b) 500 mg (4.09 mmol) of 3-ethyl-phenol were converted into 135 mg of the title compound. The compound was obtained as a light yellow liquid. $^{1H}$NMR (CDCl$_3$, 300 MHz): δ 1.28 (t, J=7.6 Hz, 3H), 2.70-2.80 (m, 4H), 2.89 (m, 2H), 3.91 (s, 2H), 6.48 (s, 1H), 7.01 (dd, J=8.2 and 2.1 Hz, 1H), 7.06 (dd, J=8.0 and 1.3 Hz, 1H), 7.27 (s, 1H), 7.28 (d, J=2.1 Hz, 1H), 7.33 (d, J=8.2 Hz, 1H), 7.41 (d, J=8.0 Hz, 1H).

EXAMPLE S12

Preparation of [2-(3,4-dichloro-phenyl)-ethyl]-(5-propyl-benzofuran-2-ylmethyl)-amine In analogy to example S7 (steps a to b) 500 mg (3.67 mmol) of 4-propyl-phenol were converted into 146 mg of the title compound. The compound was obtained as a yellow oil. $^1H$NMR (CDCl$_3$, 300 MHz): δ 0.95 (t, J=7.4 Hz, 3H), 1.66 (sext, J=7.4 Hz, 2H), 2.66 (t, J=7.4 Hz, 2H), 2.77 (m, 2H), 2.90 (m, 2H), 3.92 (s, 2H), 6.47 (s, 1H), 7.02 (dd, J=8.2 and 2.1 Hz, 1H), 7.06 (dd, J=8.4 and 1.7 Hz, 1H), 7.29 (m, 2H), 7.33 (d, J=8.4 Hz, 2H).

EXAMPLE S13

Preparation of (6-chloro-benzo[b]thiophen-2-ylmethyl)-[2-(3,4-dichloro-phenyl)-ethyl]-amine To a solution of 600 mg (3.23 mmol) of 4-chloro-2-nitrobenzaldehyde in DMF (7 ml) were added 559 mg (4.04 mmol) of potassium carbonate and 294 µl (3.23 mmol) of methyl thioglycolate at 0° C. The reaction mixture was stirred for 30 min at 0° C. and then for 24 h at RT. Then the mixture was poured into ice-water and the precipitate was collected by filtration and dissolved in ethyl acetate. The solution was dried (MgSO$_4$) and concentrated to yield 630 mg (86%) of 6-chloro-benzo[b]thiophene-2-carboxylic acid methyl ester as a white solid. $^1H$NMR (CDCl$_3$, 300 MHz): δ 3.95 (s, 3H), 7.88 (dd, J=8.6 and 1.9 Hz, 1H), 7.79 (d, J=8.6 Hz, 1H), 7.85 (d, J=1.9 Hz, 1H), 8.02 (s, 1H).

To a solution of 630 mg (2.78 mmol) of 6-chloro-benzo[b]thiophene-2-carboxylic acid methyl ester in THF (5 ml) were added 6.95 ml of 1N LiOH-solution and the reaction mixture was stirred at RT for 4 h. The pH was then adjusted to 2-3 by addition of 1N HCl and the mixture was extracted with ethyl acetate. The combined organic extracts were washed with brine, dried (MgSO$_4$) and concentrated to yield 579 mg (98%) of 6-chloro-benzo[b]thiophene-2-carboxylic acid as white solid. MS (ISP) 211.0 (M−H)$^-$.

In analogy to example S3 (steps a to b) 139 mg (0.65 mmol) of 6-chloro-benzo[b]thiophen-2-carboxylic acid were converted into 52 mg (0.14 mmol) of (6-chloro-benzo[b]thiophen-2-ylmethyl)-[2-(3,4-dichloro-phenyl)-ethyl]-amine. The product was obtained as colorless liquid. MS (ISP) 370.0 (M+H)$^+$.

EXAMPLE S14

Preparation of [2-(3,4-dichloro-phenyl)-ethyl]-(6-trifluoromethyl-benzofuran-2-ylmethyl)-amine To a solution of 600 mg (2.91 mmol) of 2-hydroxy-4-trifluoromethyl-benzoic acid in THF (3 ml) were added dropwise 5.82 ml of a 1 molar solution of BH$_3$-THF complex in THF at 0° C. After the reaction mixture was stirred for 18 h at RT, water was added to destroy excess reducing agent. Then 15 ml of 2N NaOH-solution were added and the mixture was stirred for 30 min. Then ether (10 ml) was added and the aqueous phase was separated. The volatile solvents of the organic phase were removed and the remaining residue was combined with the aqueous phase. The pH of the aqueous phase was then carefully adjusted to 6-7 by addition of dilute acetic acid at 0° C. and the mixture was extracted with ether. The combined extracts were then dried (MgSO$_4$) and concentrated to yield 649 mg (93%) of crude 2-hydroxymethyl-5-trifluoromethyl-phenol (purity ~80%) as a light yellow oil. MS (ISP) 191.2 (M−H)$^-$.

To a solution of 649 mg of 2-hydroxymethyl-5-trifluoromethyl-phenol (obtained in step a) were added 2 g of manganese dioxide and the mixture was stirred at RT for 16 h. After filtration, the filtrate was concentrated and purified by column chromatography (silica gel; cyclohexane/ethyl acetate 4:1). 2-Hydroxy-4-trifluoromethyl-benzaldehyde was isolated as a light yellow solid (292 mg, 57%). MS (ISP) 189.2 (M−H)$^-$.

In analogy to example S6 (steps a to c) 220 mg (1.16 mmol) 2-hydroxy-4-trifluoromethyl-benzaldehyde were converted into 275 mg of [2-(3,4-dichloro-phenyl)-ethyl]-(6-trifluoromethyl-benzofuran-2-ylmethyl)-amine. The compound was obtained as a dark brown oil. MS (ISP) 388.2 (M+H)$^+$.

EXAMPLE S15

Preparation of (5-chloro-benzo[b]thiophen-2-ylmethyl)-[2-(3,4-dichloro-phenyl)-ethyl]-amine In analogy to example S13) 600 mg (3.23 mmol) of 5-chloro-2-nitro-benzaldehyde were converted into 76 mg of the title compound. The compound was obtained as an off-white solid. MS (ISP) 370.0 (M+H)$^+$.

EXAMPLE S16

Preparation of [2-(3,4-dichloro-phenyl)-ethyl]-(6-methyl-4,5,6,7-tetrahydro-benzo[b]thiophen-2-ylmethyl)-amine To a solution of 446 µl (5.80 mmol) of DMF in 5 ml trichloroethylene were added 449 µl (4.90 mmol) of phosphorus oxychloride at 4° C. The mixture was then allowed to warm to RT and a solution of 500 mg (4.46 mmol) of 3-methyl-cyclohexanone in 5 ml trichloroethylene was added dropwise. After heating to 60° C. for 4 h, the reaction mixture was cooled to RT and 10 ml of a cold sodium acetate solution were added. The organic layer was separated and the aqueous phase was extracted with dichloromethane. The combined organic layers were then washed with brine, dried (MgSO$_4$) and concentrated to yield 769 mg of crude 2-chloro-4-methyl-cyclohex-1-enecarbaldehyde (containing 10% of 2-chloro-6-methyl-cyclohex-1-enecarbaldehyde) as a light yellow oil.

769 mg of the crude 2-chloro-4-methyl-cyclohex-1-enecarbaldehyde obtained in step a) were dissolved in DMF (10 ml). Then 837 mg (6.06 mmol) of potassium carbonate and 440 µl (4.85 mmol) of methyl thioglycolate were added and the mixture was heated to 100° C. for 16 h. After cooling to RT, the solvent was removed in vacuo. Water was added to the remaining residue and the mixture was extracted with ethyl acetate. The organic extracts were then washed with 50% sodium chloride solution, dried (MgSO$_4$) and concentrated to give 704 mg of 6-methyl-4,5,6,7-tetrahydro-benzo[b]thiophene-2-carboxylic acid methyl ester (containing 10% of 4-methyl-4,5,6,7-tetrahydro-benzo[b]thiophene-2-carboxylic acid methyl ester) as dark brown oil. MS (ISP) 211.1 (M+H)$^+$.

To a solution of 704 mg of 6-methyl-4,5,6,7-tetrahydro-benzo[b]thiophene-2-carboxylic acid methyl ester (obtained in step b) in a mixture of THF (5ml) and methanol (2 ml) were added 8.37 ml of 1N LiOH and the reaction mixture was stirred at RT for 16 h. Then the pH was adjusted to 2 by addition of 2N HCl and the suspension was extracted with ethyl acetate. The combined organic extracts were washed with brine, dried (MgSO$_4$) and concentrated. The remaining residue was then purified by crystallization from hot dichloromethane to give 574 mg (87%) of 6-methyl-4,5,6,7-tetrahydro-benzo[b]thiophene-2-carboxylic acid as brown solid. MS (ISP) 195.1 (M−H)⁻.

In analogy to example S2 (steps a to b) 228 mg (1.16 mmol) of 6-methyl-4,5,6,7-tetra-hydro-benzo[b]thiophene-2-carboxylic acid were converted into 298 mg (0.76 mmol) of [2-(3,4-dichloro-phenyl)-ethyl]-(6-methyl-4,5,6,7-tetrahydro-benzo[b]thiophen-2-ylmethyl)-amine. The product was obtained as colorless oil. MS (ISP) 354.0 (M+H)⁺.

EXAMPLE S17

Preparation of [2-(3,4-dichloro-phenyl)-ethyl]-(6-trifluoromethyl-4,5,6,7-tetrahydro-benzo[b]thiophen-2-ylmethyl)-amine In analogy to example S16) 500 mg (3.01 mmol) of 3-(trifluoromethyl)-cyclohexanone were converted into 246 mg of the title compound. The compound was obtained as a light yellow oil. MS (ISP) 408.1 (M+H)⁺.

EXAMPLE S18

Preparation of [2-(3,4-dichloro-phenyl)-ethyl]-(5-methyl-4,5,6,7-tetrahydro-benzo[b]thiophen-2-ylmethyl)-amine In analogy to example S16) 500 mg (4.46 mmol) of 4-methyl-cyclohexanone were converted into 232 mg of the title compound. The compound was obtained as a colorless oil. MS (ISP) 354.0 (M+H)⁺.

EXAMPLE S19

Preparation of [2-(3,4-dichloro-phenyl)-ethyl]-(5-ethyl-4,5,6,7-tetrahydro-benzo[b]thiophen-2-ylmethyl)-amine In analogy to example S16) 500 mg (3.96 mmol) of 4-ethyl-cyclohexanone were converted into 264 mg of the title compound. The compound was obtained as an orange oil. MS (ISP) 367.9 (M+H)⁺.

EXAMPLE S20

Preparation of [2-(3,4-dichloro-phenyl)-ethyl]-(5,5-dimethyl-4,5,6,7-tetrahydro-benzo[b]thiophen-2-ylmethyl)-amine In analogy to example S16) 500 mg (3.96 mmol) of 4,4-dimethyl-cyclohexanone were converted into 227 mg of the title compound. The compound was obtained as a light yellow oil. MS (ISP) 367.9 (M+H)⁺.

EXAMPLE S21

Preparation of [2-(3,4-dichloro-phenyl)-ethyl]-(6-ethyl-4,5,6,7-tetrahydro-benzo[b]thiophen-2-ylmethyl)-amine In analogy to example S16) 500 mg (3.96 mmol) of 3-ethyl-cyclohexanone were converted into 189 mg of the title compound. The compound was obtained as a light yellow oil. MS (ISP) 367.9 (M+H)⁺.

EXAMPLE S22

Preparation of [2-(3,4-dichloro-phenyl)-ethyl]-(6,6-dimethyl-4,5,6,7-tetrahydro-benzo[b]thiophen-2-ylmethyl)-amine In analogy to example S16) 500 mg (3.96 mmol) of 3,3-dimethyl-cyclohexanone were converted into 144 mg of the title compound. The compound was obtained as a light yellow oil. MS (ISP) 367.9 (M+H)⁺.

EXAMPLE S23

Preparation of 5-chloro-2-ethylamino-benzoic acid

To a solution of 1 g (5.06 mmol) of 6-chloro-1H-benzo[d][1,3]oxazine-2,4-dione in DMF (20 ml) were carefully added 265 mg of sodium hydride (55% in mineral oil) at 0° C. This mixture was stirred for 30 min at RT and then 1.18 ml (7.59 mmol) of ethyl iodide were added. Stirring was continued for 16 h at RT, then water was added and the mixture was extracted with ethyl acetate. The combined organic extracts were washed with brine, dried (MgSO₄) and concentrated. The remaining residue was purified by crystallization from heptane to obtain 682 mg (60%) of 6-chloro-1-ethyl-1H-benzo[d][1,3]oxazine-2,4-dione as an off-white solid. $^{1H}$NMR (DMSO-d₆, 300 MHz): δ 1.21 (t, J=7.0 Hz, 3H), 4.05 (q, J=7.0 Hz, 2H), 7.54 (d, J=9.1 Hz, 1H), 7.88 (dd, J=9.1 and 2.5 Hz, 1H), 7.96 (d, J=2.5 Hz, 1H).

150 mg (0.67 mmol) of 6-chloro-1-ethyl-1H-benzo[d][1,3]oxazine-2,4-dione were suspended in 1.33 ml of 2N KOH and the mixture was heated to 95° C. for 2 h. After cooling to RT the pH was adjusted to 5-6 by careful addition of 1N HCl. The precipitate was then filtered off, washed with water and dried to give 93 mg (71%) of 5-chloro-2-ethylamino-benzoic acid as a yellow solid. $^{1H}$NMR (DMSO-d₆, 300 MHz): δ 1.13 (t, J=7.2 Hz, 3H), 3.12 (q, J=7.2 Hz, 2H), 6.68 (d, J=9.1 Hz, 1H), 7.31 (dd, J=9.1 and 2.7 Hz, 1H), 7.64 (d, J=2.7 Hz, 1H).

EXAMPLE S24

Preparation of 5-chloro-2-cyclopropylamino-benzoic acid 500 mg (2.91 mmol) of 2-amino-5-chlorobenzoic acid were dissolved in methanol (25 ml) and then 3 Å molsieves, 1.67 ml of acetic acid and 2.34 ml (11.66 mmol) of (1-ethoxy-cyclo-propoxy)-trimethyl-silane were added. The mixture was stirred for 30 min at RT, then 916 mg (14.57 mmol) of sodium cyanoborohydride were added and the reaction mixture was heated to reflux for 16 h.

After cooling to RT the solids were filtered off and the volatiles were removed in vacuo. The remaining residue was dissolved in ethyl acetate and this solution was washed with 1N HCl and brine, dried (MgSO₄) and concentrated to give 312 mg of crude 5-chloro-2-cyclo-propylamino-benzoic acid as a yellow solid which was used for further reactions without additional purification. $^{1H}$NMR (DMSO-d₆, 300 MHz): δ 0.46 (m, 2H), 0.79 (m, 2H), 3.43 (m, 1H), 7.10 (d, J=8.7 Hz, 1H), 7.44 (d, J=8.7 Hz, 1H), 7.70 (s, 1H), 7.89 (br s, 1H), 13.06 (br s, 1H).

EXAMPLE S25

Preparation of (6,6-dimethyl-4,5,6,7-tetrahydro-benzo[b]thiophen-2-ylmethyl)-[2-(4-fluoro-phenyl)-ethyl]-amine The title compound was prepared in analogy to [2-(3,4-dichloro-phenyl)-ethyl]-(6,6-di-methyl-4,5,6,7-tetrahydro-benzo[b]thiophen-2-ylmethyl)-amine (example S22) and was obtained as a yellow oil. MS (ISP) 332.1 (M+H)$^+$.

EXAMPLE S26

Preparation of (6,6-dimethyl-4,5,6,7-tetrahydro-benzo[b]thiophen-2-ylmethyl)-[2-(3-trifluoromethyl-phenyl)-ethyl]-amine The title compound was prepared in analogy to [2-(3,4-dichloro-phenyl)-ethyl]-(6,6-di-methyl-4,5,6,7-tetrahydro-benzo[b]thiophen-2-ylmethyl)-amine (example S22) and was obtained as a yellow oil. MS (ISP) 368.1 (M+H)$^+$.

EXAMPLE S27

Preparation of [2-(3,4-dichloro-phenyl)-ethyl]-(6,6-dimethyl-4,5,6,7-tetrahydro-benzothiazol-2-ylmethyl)-amine 1.71 g (10.7 mmol) of bromine were added in one portion to a solution of 1.35 g (10.7 mmol) of 4,4-dimethyl-cyclohexanone in methanol (10 ml) at −10° C. The reaction mixture was then stirred for 10 min at −10° C., for 30 min at 0° C. and finally for 8 h at RT. The reaction was then quenched by addition of water (5 ml) and stirred overnight at RT. Additional water was added (20 ml) leading to the formation of a precipitate that was collected by filtration. The crude 2-bromo-4,4-dimethyl-cyclohexanone (1.72 g, 78%) that was obtained as an orange solid was used in the next reaction step without further purification. $^{1H}$NMR (CDCl$_3$, 300 MHz): δ 1.09 (s, 3H), 1.23 (s, 3H), 1.75 (m, 2H), 2.09 (t, J=13.1 Hz, 1H), 2.34 (ddd, J=13.3 and 6.1 and 2.8 Hz, 1H), 2.59 (m, 2H), 4.77 (dd, J=12.9 and 5.9 Hz, 1H).

To a solution of 1.69 g (8.24 mmol) of the crude 2-bromo-4,4-dimethyl-cyclohexanone (obtained in step a) in ethanol (10 ml) were added 1.56 g (8.24 mmol) of ethyl thiooxamate at 0° C. and the reaction mixture was then heated to reflux for 2.5 h. After cooling to RT the mixture was filtered, the filtrate was concentrated and sat. sodium carbonate solution was added to the remaining residue. This mixture was extracted with dichloromethane and the combined extracts were washed with brine, dried (MgSO$_4$) and concentrated. The crude material was then purified by column chromatography (silica gel; 100% heptane to heptane/ethyl acetate 5:1) to yield 237 mg (12%) of 6,6-dimethyl-4,5,6,7-tetrahydro-benzothiazole-2-carboxylic acid ethyl ester as a yellow oil. MS (ISP) 240.2 (M+H)$^+$.

1.37 ml of 1N lithium hydroxide solution were added to a solution of 235 mg (0.98 mmol) of 6,6-dimethyl-4,5,6,7-tetrahydro-benzothiazole-2-carboxylic acid ethyl ester in THF (1 ml) and the mixture was stirred at RT for 2.5 h. Then all volatiles were removed under reduced pressure to yield 230 mg (92%) of the lithium salt of 6,6-dimethyl-4,5,6,7-tetrahydro-benzothiazole-2-carboxylic acid as a yellow solid.

In analogy to example S2 (steps a to b) 230 mg (0.98 mmol) of the lithium salt of 6,6-dimethyl-4,5,6,7-tetrahydro-benzothiazole-2-carboxylic acid were converted into 23 mg (0.06 mmol) of [2-(3,4-dichloro-phenyl)-ethyl]-(6,6-dimethyl-4,5, 6,7-tetrahydro-benzothiazol-2-ylmethyl)-amine. The product was obtained as a yellow oil. MS (ISP) 368.8 (M+H)$^+$.

EXAMPLE S28

Preparation of (5,5-dimethyl-4,5,6,7-tetrahydro-benzo[b]thiophen-2-ylmethyl)-[2-(4-fluoro-phenyl)-ethyl]-amine The title compound was prepared in analogy to [2-(3,4-dichloro-phenyl)-ethyl]-(5,5-di-methyl-4,5,6,7-tetrahydro-benzo[b]thiophen-2-ylmethyl)-amine (example S20) and was obtained as a yellow oil. MS (ISP) 318.1 (M+H)$^+$.

EXAMPLE S29

Preparation of (5,5-dimethyl-4,5,6,7-tetrahydro-benzo[b]thiophen-2-ylmethyl)-[2-(3-trifluoromethyl-phenyl)-ethyl]-amine The title compound was prepared in analogy to [2-(3,4-dichloro-phenyl)-ethyl]-(5,5-di-methyl-4,5,6,7-tetrahydro-benzo[b]thiophen-2-ylmethyl)-amine (example S20) and was obtained as a yellow oil. MS (ISP) 368.3 (M+H)$^+$.

EXAMPLE S30

Preparation of 5-chloro-6-fluoro-1H-indole-7-carboxylic acid 10 g (68.7 mmol) of 4-chloro-3-fluoro-phenylamine were dissolved in 38 ml dichloro-methane and treated with a solution of 6.82 g (72.1 mmol) of sodium bicarbonate in water (110 ml). At RT 8 ml (103 mmol) of methyl chloroformate were added dropwise over a period of 25 min (temperature rise from 22 to 28° C.). After stirring for 1.5 h at RT, the reaction mixture was diluted with dichloromethane (100 ml). After phase separation, the organic layer was washed with brine (45 ml), dried with magnesium sulfate, filtered and diluted with hexane (140 ml). The dichloromethane was then removed in vacuo and the resulting suspension filtered leading to 13 g (4-chloro-3-fluoro-phenyl)-carbamic acid methyl ester as a white powder (92%). MS (EI) 203.1 (M)$^+$.

5.34 g (26.2 mmol) of (4-chloro-3-fluoro-phenyl)-carbamic acid methyl ester were dissolved in acetonitrile (50 ml) and treated with 6.49 g (28.85 mmol) of N-iodosuccinimide and 0.23 ml (2.62 mmol) of trifluoromethanesulfonic acid under nitrogen and stirred at RT for 3 hours. The reaction mixture was then poured into 50 ml of saturated sodium bicarbonate solution and extracted twice with ethyl acetate. The combined organic extracts were then washed with brine, dried with magnesium sulfate, filtered and concentrated in vacuo, leading to 8.2 g of (4-chloro-5-fluoro-2-iodo-phenyl)-carbamic acid methyl ester (95%) as a dark blue powder. MS (EI) 328.9 (M)$^+$.

153 mg (0.22 mmol) of Pd(PPh$_3$)$_2$Cl$_2$ and 42 mg (0.22 mmol) of CuI were dissolved in 40 ml of triethylamine under argon and the mixture was heated to reflux for 20 min. The reaction mixture was then cooled to 0° C. and 7.2 g (21 mmol) of (4-chloro-5-fluoro-2-iodo-phenyl)-carbamic acid methyl ester were added. After 10 min stirring at RT, 3.45 ml (24.9 mmol) of ethynyltrimethylsilane were added dropwise (exothermic, temperature rise from 18 to 33° C.) and the reaction mixture was stirred for one hour at RT. The mixture was then poured into 180 ml of aqueous 1N HCl and ice and extracted with ethyl acetate. The organic extracts were then washed with water and brine, dried with magnesium sulfate, filtered and concentrated in vacuo. The remaining crude material (ca 21 mmol) was dissolved in THF (200 ml) and treated with 43.3 ml (43.3 mmol) of tetrabutylammonium fluoride (1M in THF) at RT. After 5 min stirring at RT, the reaction mixture was refluxed for one hour under argon. The reaction mixture was then cooled to RT and concentrated in vacuo. The resulting oil was treated with water (55 ml), stirred for 10 min and finally extracted with ethyl acetate. The combined organic layers were sequentially washed with 1M HCl (50 ml), saturated sodium bicarbonate (50 ml), brine (50 ml) and finally dried with magnesium sulfate, filtered and concentrated in vacuo. The remaining residue was suspended in hexane (200 ml) and the mixture was heated to reflux, then cooled to 5° C. and the solid was collected by filtration leading to 3.15 g of 5-chloro-6-fluoro-1H-indole as a light brown solid (85%). MS (EI) 169.1 (M)⁺.

35 ml of THF were cooled to −75° C. and 19.05 ml (30.5 mmol) of a 1.6M solution of n-butyllithium in hexane were added under argon. Then a solution of 2.35 g (13.7 mmol) of 5-chloro-6-fluoro-1H-indole in THF (9 ml) was added dropwise (temperature kept between −70 and −75° C.) over 15 min. After 5 additional min of stirring at this temperature a solution of 3.7 g of potassium tert-butylate in THF (15 ml) was added over period of 10 min (temperature kept between −70 and −75° C.). The resulting brown solution was then stirred for 2 hours at the same temperature and treated with a large excess of solid $CO_2$. The temperature was then raised to 10° C. over a period of 75 min and water (30 ml) was added to the reaction mixture. After separation of the organic layer, the aqueous layer was extracted with ether and treated with concentrated HCl to adjust the pH to 1. The resulting suspension was then filtered and the solid was washed with water and dried in high vacuo. The remaining residue was suspended in 10 ml of hexane/ether 9:1 and stirred for 15 min, filtered off, washed with 5 ml of the same solvent mixture and was dried in high vacuo, leading to 2.2 g of 5-chloro-6-fluoro-1H-indole-7-carboxylic acid as a light brown solid (75%). MS: 212.2 (M−H)⁻

EXAMPLE S31

Preparation of 2-chloro-5-methylamino-isonicotinic acid n-Butyllithium (1.6 M in hexane, 6.78 mL, 10.8 mmol) was added at −78° C. to a solution of (6-chloro-4-iodo-pyridin-3-yl)-methyl-carbamic acid tert-butyl ester (synthesized according to WO 2005002577; 2.00 g, 5.43 mmol) in THF (40 mL). After 15 min the solution was purged with carbon dioxide gas for 15 min, then allowed to reach RT. The reaction mixture partitioned between hexane and water and the organic layer was extracted with 1% aq. ammonia solution. The combined aqueous layer was washed with hexane/ethyl acetate 1:1, and the pH was set to 4 by addition of 1 M aq. hydrochloric acid solution. The precipitate was collected by filtration and washed with water, to afford 5-(tert-butoxycarbonyl-methyl-amino)-2-chloro-isonicotinic acid (1.28 g, 83%). Yellow solid, MS (ISP): 287.1 (M+H)⁺.

5-(tert-Butoxycarbonyl-methyl-amino)-2-chloro-isonicotinic acid (1.04 g, 3.63 mmol) was converted into 2-chloro-5-methylamino-isonicotinic acid (625 mg, 92%) by heating at 240° C. in a Kugelrohr apparatus for 10 min. Yellow solid, MS (ISP): 187.1 (M+H)⁺.

EXAMPLE S32

Preparation of (6-tert-butyl-pyridin-3-ylmethyl)-[2-(3,4-dichloro-phenyl)-ethyl]-amine In analogy to example S1, the title compound was obtained from 6-tert-butyl-pyridine-3-carbaldehyde (synthesized according to *J. Med. Chem.* 2005, 48, 71-90) and 2-(3,4-dichloro-phenyl)-ethylamine. Light yellow oil, MS (ISP): 337.4 (M+H)⁺.

EXAMPLE S33

Preparation of (6-tert-butyl-pyridin-3-ylmethyl)-[2-(3-trifluoromethyl-phenyl)-ethyl]-amine In analogy to example S1, the title compound was obtained from 6-tert-butyl-pyridine-3-carbaldehyde and 2-(3-trifluoromethyl-phenyl)-ethylamine. Light yellow oil, MS (ISP): 337.4 (M+H)⁺.

EXAMPLE S34

Preparation of (6-tert-butyl-pyridin-3-ylmethyl)-[2-(4-chloro-phenyl)-ethyl]-amine In analogy to example S1, the title compound was obtained from 6-tert-butyl-pyridine-3-carbaldehyde and 2-(4-chloro-phenyl)-ethylamine. Light yellow oil, MS (ISP): 303.1 (M+H)⁺.

EXAMPLE S35

Preparation of (5-tert-butyl-pyridin-2-ylmethyl)-[2-(3,4-dichloro-phenyl)-ethyl]-amine Potassium hydroxide (2 M aq. solution, 0.98 mL, 1.96 mmol) was added at RT to a solution of 5-tert-butyl-pyridine-2-carboxylic acid methyl ester (synthesized according to *J. Org. Chem.* 1998, 63, 7840-7850; 189 mg, 0.98 mmol) in THF (2.6 mL), then after stirring for 2 h, the reaction mixture was evaporated. The residue was taken up in DMF (12 mL), then after addition of 2-(3,4-dichloro-phenyl)-ethylamine (204 mg, 1.07 mmol), 4-methylmorpholine (297 mg, 2.93 mmol), and HBTU (556 mg, 1.47 mmol), the reaction mixture was stirred at RT for 16 h, then partitioned between water and ethyl acetate. The organic layer was washed with brine, dried ($MgSO_4$), and concentrated. Chromatography ($SiO_2$, heptane-ethyl acetate gradient) produced 5-tert-butyl-pyridine-2-carboxylic acid [2-(3,4-dichloro-phenyl)-ethyl]-amide (200 mg, 58%). White solid, MS (ISP): 351.4 (M+H)⁺.

Diisobutylaluminum hydride (1 M solution in THF, 0.40 mL, 0.40 mmol) was added dropwise to a solution of 5-tert-butyl-pyridine-2-carboxylic acid [2-(3,4-dichloro-phenyl)-ethyl]-amide (195 mg, 0.555 mmol) in THF (2 mL) at 0° C., then after 15 min, the reaction was stopped by careful addition of water. The reaction mixture was partitioned between ethyl acetate and 1 M aq. potassium sodium tartrate solution, the organic layer was washed with brine, dried ($MgSO_4$), and concentrated. Chromatography ($SiO_2$, heptane/ethyl acetate 1:1, then dichloromethane/methanol 9:1) afforded (5-tert-butyl-pyridin-2-ylmethyl)-[2-(3,4-dichloro-phenyl)-ethyl]-amine (128 mg, 68%). Yellow oil, MS (ISP): 337.3 (M+H)⁺.

EXAMPLE S36

Preparation of (5-tert-butyl-pyridin-2-ylmethyl)-[2-(3-trifluoromethyl-phenyl)-ethyl]-amine In analogy to example S35, the title compound was obtained from 5-tert-butyl-pyridine-2-carboxylic acid methyl ester and 2-(3-trifluoromethyl-phenyl)-ethylamine. Light yellow oil, MS (ISP): 337.4 (M+H)$^+$.

EXAMPLE S37

Preparation of (5-tert-butyl-thiophen-2-ylmethyl)-[2-(3-trifluoromethyl-phenyl)-ethyl]-amine In analogy to example S3 (steps a to b) 300 mg (1.63 mmol) of 5-tert-butyl-thiophene-2-carboxylic acid were converted into 483 mg (1.42 mmol) of (5-tert-butyl-thiophen-2-ylmethyl)-[2-(3-trifluoromethyl-phenyl)-ethyl]-amine. The product was obtained as a colorless oil. MS (ISP) 342.0 (M+H)$^+$.

EXAMPLE S38

Preparation of (4-tert-butyl-thiazol-2-ylmethyl)-[2-(3-trifluoromethyl-phenyl)-ethyl]-amine To a solution of 1.8 g (10.05 mmol) of 1-bromopinacolone in 15 ml of ethanol were added 1.41 g (10.05 mmol) of ethyl thiooxamate at 0° C. Then the mixture was heated to reflux for 1.5 h and after cooling to RT the reaction mixture was concentrated. Then sat. NaHCO$_3$-solution was added and the mixture was extracted twice with ethyl acetate. The combined organic layers were dried (Na$_2$SO$_4$) and concentrated to yield 2.1 g (98%) of 4-tert-butyl-thiazole-2-carboxylic acid ethyl ester as a yellow oil. MS (ISP) 214.3 (M+H)$^+$.

640 mg (3.00 mmol) of 4-tert-butyl-thiazole-2-carboxylic acid ethyl ester were dissolved in 1.5 ml of THF and 4.5 ml of a 1N LiOH solution were added. The reaction mixture was stirred at RT for 2 h. Then all volatiles were removed and the residue containing the lithium salt of 4-tert-butyl-thiazole-2-carboxylic acid was used in the next reaction step without further purification. MS (ISP) 184.1 (M–H)$^-$.

In analogy to example S3 (steps a to b) 345 mg of the lithium salt of 4-tert-butyl-thiazole-2-carboxylic acid obtained in step b) were converted into 315 mg (0.92 mmol) of (4-tert-butyl-thiazol-2-ylmethyl)-[2-(3-trifluoromethyl-phenyl)-ethyl]-amine. The product was obtained as viscous yellow oil.

EXAMPLE S39

Preparation of (4-tert-butyl-thiazol-2-ylmethyl)-[2-(4-chloro-phenyl)-ethyl]-amine The title compound was prepared in analogy to example S38 and was obtained as viscous yellow oil. MS (ISP) 309.3 (M+H)$^+$.

EXAMPLE S40

Preparation of 5-chloro-2-methylamino-benzoic acid

The title compound was prepared in analogy to example S23 and was obtained as a yellow solid. MS (ISP) 183.9 (M–H)$^-$.

The compounds of formula I are cholesteryl ester transfer protein (CETP) inhibitors.

Atherosclerosis and its associated coronary heart disease is the leading cause of death in the industrialized world. Risk for development of coronary heart disease has been shown to be strongly correlated with certain plasma lipid levels. Lipids are transported in the blood by lipoproteins. The general structure of lipoproteins is a core of neutral lipids (triglyceride and cholesterol ester) and an envelope of polar lipids (phospholipids and non esterified cholesterol). There are three different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

Plasma lipoprotein metabolism can be described as a flux of cholesterol between liver and the other tissues. The LDL pathway corresponds to the secretion of VLDL from the liver to deliver cholesterol by LDL to tissues. Any alteration in LDL catabolism could lead to uptake of excess cholesterol in the vessel wall forming foam cells and atherosclerosis. The opposite pathway is the mobilization of free cholesterol from peripheral tissues by HDL to deliver cholesterol to the liver to be eventually excreted with bile. In humans a significant part of cholesteryl ester (CE) is transferred from HDL to the VLDL, LDL pathway. This transfer is mediated by a 70,000 dalton plasma glycoprotein, the cholesteryl ester transfer protein (CETP).

Mutations in the CETP gene associated with CETP deficiency are characterized by high HDL-cholesterol levels (>60 mg/dL) and reduced cardiovascular risk. Such findings are consistent with studies of pharmacologically mediated inhibition of CETP in the rabbit, which argue strongly in favor of CETP inhibition as a valid therapeutic approach [Le Goff et al., Pharmacology & Therapeutics 101:17-38 (2004); Okamoto et al., Nature 406:203-207 2000)].

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (-10-12%). As a result, there is a significant unmet medical need for a well tolerated agent which can significantly elevate plasma HDL levels. The net result of CETP activity is a lowering of HDL-C and an increase in LDL-C. This effect on lipoprotein profile is believed to be pro-atherogenic, especially in subjects whose lipid profile constitutes an increased risk for coronary heart disease. Therefore by inhibiting CETP activity there is the potential to inverse this relationship towards a lower risk and ultimately to protect against coronary heart diseases and associated mortality.

Thus, CETP inhibitors are useful as medicaments for the treatment and/or prophylaxis of atherosclerosis, peripheral vascular disease, dyslipidemia, hyperbeta-lipoproteinemia, hypoalphalipoproteinemia, hypercholesterolemia, hypertriglyceridemia, familial hyper-cholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In addition, CETP inhibitors may be used in combination with another compound, said compound being an HMG-CoA reductase inhibitor, a microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant.

As described above, the compounds of formula I of the present invention can be used as medicaments for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use as medicament for the treatment and/or prevention of dyslipidemia is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In another embodiment, the invention relates to a method for the treatment and/or pro-phylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. A method for the treatment and/or prophylaxis of dyslipidemia is preferred.

The invention further relates to the use of compounds of formula I as defined above for the treatment and/or prophylaxis of diseases are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the treatment and/or prophylaxis of dyslipidemia is preferred.

In addition, the invention relates to the use of compounds of formula I as defined above for the preparation of medicaments for the treatment and/or prophylaxis of diseases are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the preparation of medicaments for the treatment and/or prophylaxis of dyslipidemia is preferred.

In addition, CETP inhibitors are useful in combination with another compound, said compound being an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant.

The invention therefore also relates to pharmaceutical compositions comprising a compound of formula I as defined above in combination with an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant, as well as a pharmaceutically acceptable carrier and/or adjuvant.

The invention further relates to the use of compounds of formula I as defined above in combination with an HMG-CoA reductase inhibitor, a microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant for the treatment and/or prophylaxis of diseases such as atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia, as well as to the use of such a combination for the preparation of corresponding medicaments.

The compounds of formula I and their pharmaceutically acceptable salts possess valuable pharmacological properties. Specifically, it has been found that the compounds of the present invention are inhibitors of the cholesteryl ester transfer protein (CETP).

The following tests were carried out in order to determine the activity of the compounds of formula I.

Activity of CETP inhibitors was determined using a buffer assay system. Partially purified CETP transferred radiolabeled cholesteryl ester from HDL donor particles to biotin-labeled LDL acceptor particles. The reaction was stopped by addition of streptavidin-coupled scintillation proximity assay (SPA) beads. These beads captured the biotinylated acceptor particles and transferred radioactivity was measured. The assay system was purchased and performed according to manufacturer's recommendations (Amersham Biosciences). Inhibitory activity of compounds was determined as percentage of positive control activity containing CETP together with donor and acceptor particles. Serial dilution of compounds was performed in order to determine the $IC_{50}$ values.

Activity of the compounds was subsequently measured in the presence of plasma using the same assay as described above except that the source of CETP was human lipoprotein-deprived serum (LPDS). Inhibitory activity of compounds was determined as percentage of positive control activity containing all the assay components except compound. Serial dilution of compounds was performed in order to determine the $IC_{50}$ values.

Under the latter assay conditions, the compounds of the present invention exhibit $IC_{50}$ values within the range of about 1 nM to about 100 µM, e.g., of about 1 nM to about 1 µM, e.g., of about 1 nM to about 200 nM. The following table shows measured values for some selected compounds of the present invention.

|  | $IC_{50}$ (nM) |
| --- | --- |
| Compound 1 | 7020 |
| Compound 53 | 56 |
| Compound 38 | 282 |

In vivo activity of the compounds of formula I were determined in hamster using the following protocol:

Male golden Syrian hamsters (6-week-old, 100-130 g) under standard chow diet received compounds in the morning by oral gavage using appropriate vehicle, blood was taken 2 h later by retro-orbital bleeding under isofuran anaesthesia and 7 h later on sacrificed animals. Plasma was separated from blood using low speed centrifugation and CETP activity was measured in plasma using the radioactive CETP activity assay as described above except that diluted plasma replaced LPDS. In vivo CETP inhibition was expressed as CETP activity remaining in the plasma of treated animals as compared to plasma CETP activity of placebo treated animals.

Efficacy of compounds in modulating plasma lipid levels can be determined in hamsters after 7 days of daily administration of compounds. Male hamsters are acclimated for 3-4 days to receive food as a paste made of 10 g chow and 10 g water per day. Compounds are then mixed within this paste and a portion containing the proper amount of compounds is given every morning for 7 days. Alternatively compounds can be given by oral gavage using the proper vehicle. Blood is taken before compound treatment by retro-orbital bleeding and at the end of the treatment on sacrificed animals. Plasma is separated from blood by low speed centrifugation and selected organs are taken (e.g liver, fat, brain, etc.). Effects of compounds on plasma lipid levels are determined by measuring total cholesterol, HDL-cholesterol, LDL-cholesterol and triglyceride using calorimetric enzymatic assays (Roche Diagnostic GmbH, Mannheim, Germany). HDL-C, LDL-C and VLDL-C are e.g., quantified using size exclusion chromatography on superpose-6 column using SMART™ system (Pharmacia). Lipoprotein distribution is calculated assuming a Gaussian distribution for each peak, using a non-linear, least-squares curve-fitting procedure to calculate the area under the curve. Plasma samples are also used to quantify CETP activity as described above. Compound concentration is also determined in plasma and selected tissues as liver, fat, heart, muscle and brain.

Efficacy of compounds in modulating plasma lipid levels can also be determined in cholesterol/fat fed hamsters. The protocol is identical as described above except that animals are fed with chow diet enriched with 10% (w/w) saturated fat and 0.05% (w/w) cholesterol. Animals receive this high fat diet 2 weeks before starting compound administration and continue this diet throughout the study. The 2 weeks pre-treatment induces an increase in plasma cholesterol and triglyceride levels allowing a better assessment of LDL-C and triglyceride lowering.

Efficacy of compounds in its ability to acutely raise HDL-C can be assessed in cynomolgus monkeys. Animals are fed with standard primate maintenance diet. Compounds are formulated with appropriate vehicle and administered to animals by oral gavage. Blood is taken before and at several timepoints after compound administration (usually 30 min, 1 h, 2 h, 4 h, 7 h and 24 h). Plasma is separated from blood by low speed centrifugation and CETP activity and plasma lipids are quantified. Compound potency and efficacy can be assessed by measuring the HDL-C increase after this single-dose administration. In such pharmacodynamic model the extent together with the kinetics of the pharmacologic effect can be assessed.

The compounds of formula I and their pharmaceutically acceptable salts and esters can be used as medicaments, e.g. in the form of pharmaceutical preparations for enteral, parenteral or topical administration. They can be administered, e.g., perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, e.g., lactose, corn starch or derivatives thereof, talc, stearic acid or its salts can be used as carrier materials for tablets, coated tablets, dragees and hard gelatine capsules. Suitable carrier materials for soft gelatine capsules are, e.g., vegetable oils, waxes, fats and semi-solid and liquid polyols (depending on the nature of the active ingredient no carriers are, however, required in the case of soft gelatine capsules). Suitable carrier materials for the production of solutions and syrups are, e.g., water, polyols, sucrose, invert sugar and the like. Suitable carrier materials for injection solutions are, e.g., water, alcohols, polyols, glycerol and vegetable oils. Suitable carrier materials for suppositories are, e.g., natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, e.g., 0.5-100 mg, of a compound of formula I.

The following examples serve to illustrate the present invention in more detail. They are, however, not intended to limit its scope in any manner.

EXAMPLE A

Film Coated Tablets

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

EXAMPLE B

Capsules

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

EXAMPLE C

Injection Solutions

| | |
| --- | --- |
| Compound of formula (I) | 3.0 mg |
| Gelatin | 150.0 mg |
| Phenol | 4.7 mg |
| Sodium carbonate | to obtain a final pH of 7 |
| Water for injection solutions | ad 1.0 ml |

EXAMPLE D

Soft Gelatin Capsules

| | |
| --- | --- |
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg |
| | (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

The invention claimed is:

1. A compound of formula (I):

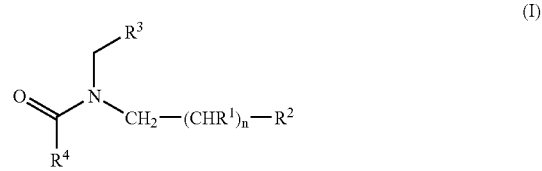

or a pharmaceutically acceptable salt thereof, wherein:
  $R^1$ is hydrogen, $C_1$-$C_6$alkyl, hydroxy or halogen;
  $R^2$ is aryl optionally substituted by one or more substituents selected from the group consisting of: halogen and halogen-$C_1$-$C_6$alkyl;
  $R^3$ is unsubstituted heteroaryl or heteroaryl substituted by one or more substituents selected from the group consisting of: halogen, $C_1$-$C_6$alkyl, halogen-$C_1$-$C_6$alkyl, $C_3$-$C_8$cycloalkyl, and halogen-$C_3$-$C_8$cycloalkyl;
  $R^4$ is a group (a)

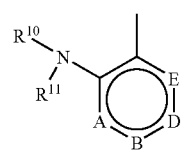

wherein:
  A is $CR^{17}$ and $R^{17}$ and $R^{11}$ together are —CH=CH—;
  B is $CR^{18}$ wherein $R^{18}$ is hydrogen, halogen, $C_1$-$C_6$alkyl, $C_1$-$C_6$alkoxy or $C_2$-$C_6$alkenyl;
  D is $CR^{19}$ wherein $R^{19}$ is hydrogen, halogen, $C_1$-$C_6$alkyl, $C_1$-$C_6$alkoxy, $C_2$-$C_6$alkenyl or phenyl;
  E is $CR^{20}$ wherein $R^{20}$ is hydrogen, halogen, $C_1$-$C_6$alkyl, $C_1$-$C_6$alkoxy or $C_2$-$C_6$alkenyl;
  $R^{10}$ is selected from the group consisting of: (1) hydrogen, (2) halogen, (3) $C_1$-$C_6$alkyl, (4) COR wherein R is C₁-C₆alkyl, C₁-C₆alkoxy or C₃-C₆cycloalkyl, (5) S(O)₂—C₁-C₆alkyl, (6) C₃-C₆cycloalkyl, and (7) phenyl; and n is 1, 2 or 3.

2. A compound according to claim 1 wherein $R^2$ is unsubstituted aryl or aryl substituted by halogen.

3. A compound according to claim 1 wherein $R^3$ is heteroaryl selected from the group consisting of: pyridinyl, thiazolyl, thiophenyl, indolyl, benzo[b]thiophenyl, 4,5,6,7-tetrahydro-benzo[b]thiophenyl, benzofuranyl, and 4,5,6,7-tetrahydro-benzothiazolyl, which said heteroaryl is unsubstituted or substituted by one or more substituents selected from the group consisting of: halogen, C₁-C₆alkyl, halogen-C₁-C₆alkyl, C₃-C₈cycloalkyl, and halogen-C₃-C₈cycloalkyl.

4. A compound according to claim 1 wherein $R^{19}$ is halogen.

5. A compound according to claim 1 wherein:
$R^1$ is hydrogen;
$R^3$ is unsubstituted heteroaryl or heteroaryl substituted by one or more substituents selected from the group consisting of halogen, C₁-C₆alkyl and halogen-C₁-C₆alkyl; and
$R^{19}$ is chloro.

6. A pharmaceutical composition comprising a compound according to claim 1 and a pharmaceutically acceptable carrier or adjuvant or mixture thereof.

7. A compound according to claim 1 selected from the group consisting of:
5-chloro-1H-indole-7-carboxylic acid benzofuran-2-ylmethyl-[2-(3,4-dichloro-phenyl)-ethyl]-amide;
5-chloro-1H-indole-7-carboxylic acid benzo[b]thiophen-2-ylmethyl-[2-(3,4-dichloro-phenyl)-ethyl]-amide;
5-chloro-1H-indole-7-carboxylic acid [2-(3,4-dichlorophenyl)-ethyl]-(6,7-dimethyl-benzofuran-2-ylmethyl)-amide;
and a pharmaceutically acceptable salt thereof.

8. A compound according to claim 1 selected from the group consisting of:
5-chloro-1H-indole-7-carboxylic acid (5,7-dichloro-benzofuran-2-ylmethyl)-[2-(3,4-dichloro-phenyl)-ethyl]-amide;
5-chloro-1H-indole-7-carboxylic acid [2-(3,4-dichlorophenyl)-ethyl]-(5-methyl-benzofuran-2-ylmethyl)-amide;
5-chloro-1H-indole-7-carboxylic acid [2-(3,4-dichlorophenyl)-ethyl]-(6-methyl-benzofuran-2-ylmethyl)-amide;
and a pharmaceutically acceptable salt thereof.

9. A compound according to claim 1 selected from the group consisting of:
5-chloro-1H-indole-7-carboxylic acid [2-(3,4-dichlorophenyl)-ethyl]-(5-methyl-benzo[b]thiophen-2-ylmethyl)-amide;
5-chloro-1H-indole-7-carboxylic acid [2-(3,4-dichlorophenyl)-ethyl]-(5-ethyl-benzofuran-2-ylmethyl)-amide;
5-chloro-1H-indole-7-carboxylic acid [2-(3,4-dichlorophenyl)-ethyl]-(5,6-dimethyl-benzofuran-2-ylmethyl)-amide;
and a pharmaceutically acceptable salt thereof.

10. A compound according to claim 1 selected from the group consisting of:
5-chloro-1H-indole-7-carboxylic acid [2-(3,4-dichlorophenyl)-ethyl]-(6-ethyl-benzofuran-2-ylmethyl)-amide;
5-chloro-1H-indole-7-carboxylic acid [2-(3,4-dichlorophenyl)-ethyl]-(5-propyl-benzofuran-2-ylmethyl)-amide;
5-chloro-1H-indole-7-carboxylic acid (6-chloro-benzo[b]thiophen-2-ylmethyl)-[2-(3,4-dichloro-phenyl)-ethyl]-amide;
and a pharmaceutically acceptable salt thereof.

11. A compound according to claim 1 selected from the group consisting of:
5-chloro-1H-indole-7-carboxylic acid [2-(3,4-dichlorophenyl)-ethyl]-(6-trifluoromethyl-benzofuran-2-ylmethyl)-amide;
5-chloro-1H-indole-7-carboxylic acid (5-chloro-benzo[b]thiophen-2-ylmethyl)-[2-(3,4-dichloro-phenyl)-ethyl]-amide;
5-chloro-1H-indole-7-carboxylic acid [2-(3,4-dichlorophenyl)-ethyl]-(6-methyl-4,5,6,7-tetrahydro-benzo[b]thiophen-2-ylmethyl)-amide;
and a pharmaceutically acceptable salt thereof.

12. A compound according to claim 1 selected from the group consisting of:
5-chloro-1H-indole-7-carboxylic acid [2-(3,4-dichlorophenyl)-ethyl]-(6-trifluoromethyl-4,5,6,7-tetrahydro-benzo[b]thiophen-2-ylmethyl)-amide;
5-chloro-1H-indole-7-carboxylic acid [2-(3,4-dichlorophenyl)-ethyl]-(5-methyl-4,5,6,7-tetrahydro-benzo[b]thiophen-2-ylmethyl)-amide;
5-chloro-1H-indole-7-carboxylic acid [2-(3,4-dichlorophenyl)-ethyl]-(5-ethyl-4,5,6,7-tetrahydro-benzo[b]thiophen-2-ylmethyl)-amide;
and a pharmaceutically acceptable salt thereof.

13. A compound according to claim 1 selected from the group consisting of:
5-chloro-1H-indole-7-carboxylic acid [2-(3,4-dichlorophenyl)-ethyl]-(5,5-dimethyl-4,5,6,7-tetrahydro-benzo[b]thiophen-2-ylmethyl)-amide;
5-chloro-1H-indole-7-carboxylic acid [2-(3,4-dichlorophenyl)-ethyl]-(6-ethyl-4,5,6,7-tetrahydro-benzo[b]thiophen-2-ylmethyl)-amide;
5-chloro-1H-indole-7-carboxylic acid [2-(3,4-dichlorophenyl)-ethyl]-(6,6-dimethyl-4,5,6,7-tetrahydro-benzo[b]thiophen-2-ylmethyl)-amide;
and a pharmaceutically acceptable salt thereof.

14. A compound according to claim 1 selected from the group consisting of:
5-chloro-1H-indole-7-carboxylic acid (6,6-dimethyl-4,5,6,7-tetrahydro-benzo[b]thiophen-2-ylmethyl)-[2-(4-fluoro-phenyl)-ethyl]-amide;
5-chloro-1H-indole-7-carboxylic acid (6,6-dimethyl-4,5,6,7-tetrahydro-benzo[b]thiophen-2-ylmethyl)-[2-(3-trifluoromethyl-phenyl)-ethyl]-amide;
5-chloro-1H-indole-7-carboxylic acid [2-(3,4-dichlorophenyl)-ethyl]-(6,6-dimethyl-4,5,6,7-tetrahydro-benzothiazol-2-ylmethyl)-amide;
and a pharmaceutically acceptable salt thereof.

15. A compound according to claim 1 selected from the group consisting of:
5-chloro-1H-indole-7-carboxylic acid (5,5-dimethyl-4,5,6,7-tetrahydro-benzo[b]thiophen-2-ylmethyl)-[2-(4-fluoro-phenyl)-ethyl]-amide;
5-chloro-1H-indole-7-carboxylic acid (5,5-dimethyl-4,5,6,7-tetrahydro-benzo[b]thiophen-2-ylmethyl)-[2-(3-trifluoromethyl-phenyl)-ethyl]-amide;
5-chloro-6-fluoro-1H-indole-7-carboxylic acid (5,5-dimethyl-4,5,6,7-tetrahydro-benzo[b]thiophen-2-ylmethyl)-[2-(4-fluoro-phenyl)-ethyl]-amide;
and a pharmaceutically acceptable salt thereof.

16. A compound according to claim 1 selected from the group consisting of:

5-chloro-6-fluoro-1H-indole-7-carboxylic acid (5,5-dimethyl-4,5,6,7-tetrahydro-benzo[b]thiophen-2-ylmethyl)-[2-(3-trifluoromethyl-phenyl)-ethyl]-amide;

5-chloro-6-fluoro-1H-indole-7-carboxylic acid [2-(3,4-dichloro-phenyl)-ethyl]-(5,5-dimethyl-4,5,6,7-tetrahydro-benzo[b]thiophen-2-ylmethyl)-amide;

5-chloro-6-fluoro-1H-indole-7-carboxylic acid (6-tert-butyl-pyridin-3-ylmethyl)-[2-(3,4-dichloro-phenyl)-ethyl]-amide;

and a pharmaceutically acceptable salt thereof.

17. A compound according to claim 1 selected from the group consisting of:

5-chloro-6-fluoro-1H-indole-7-carboxylic acid (6-tert-butyl-pyridin-3-ylmethyl)-[2-(3-trifluoromethyl-phenyl)-ethyl]-amide;

5-chloro-6-fluoro-1H-indole-7-carboxylic acid (5-tert-butyl-pyridin-2-ylmethyl)-[2-(3-trifluoromethyl-phenyl)-ethyl]-amide;

5-chloro-6-fluoro-1H-indole-7-carboxylic acid (6-tert-butyl-pyridin-3-ylmethyl)-[2-(4-chloro-phenyl)-ethyl]-amide;

and a pharmaceutically acceptable salt thereof.

18. A compound according to claim 1 selected from the group consisting of:

5-chloro-6-fluoro-1H-indole-7-carboxylic acid (5-tert-butyl-thiophen-2-ylmethyl)-[2-(3-trifluoromethyl-phenyl)-ethyl]-amide;

5-chloro-6-fluoro-1H-indole-7-carboxylic acid (4-tert-butyl-thiazol-2-ylmethyl)-[2-(3-trifluoromethyl-phenyl)-ethyl]-amide;

and a pharmaceutically acceptable salt thereof.

19. A compound according to claim 1 which is 5-chloro-1H-indole-7-carboxylic acid (6,6-dimethyl-4,5,6,7-tetrahydro-benzo[b]thiophen-2-ylmethyl)-[2-(4-fluoro-phenyl)-ethyl]-amide.

20. A compound according to claim 1 which is 5-chloro-1H-indole-7-carboxylic acid (6,6-dimethyl-4,5,6,7-tetrahydro-benzo[b]thiophen-2-ylmethyl)-[2-(3-trifluoromethyl-phenyl)-ethyl]-amide.

* * * * *